(12) United States Patent
Horwitz et al.

(10) Patent No.: US 6,541,509 B2
(45) Date of Patent: Apr. 1, 2003

(54) METHOD FOR TREATING NEOPLASIA USING COMBINATION CHEMOTHERAPY

(75) Inventors: Susan B. Horwitz, Larchmont, NY (US); Hayley M. McDaid, Bronx, NY (US); Laura A. Martello, Franklin Square, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/953,585

(22) Filed: Sep. 14, 2001

(65) Prior Publication Data

US 2002/0065234 A1 May 30, 2002

Related U.S. Application Data

(60) Provisional application No. 60/233,191, filed on Sep. 15, 2000.

(51) Int. Cl.$^7$ ............................................. A61K 31/335
(52) U.S. Cl. ........................ 514/449; 514/459; 514/460; 514/922; 514/908
(58) Field of Search ................................ 514/449, 459, 514/460, 908, 922

(56) References Cited

U.S. PATENT DOCUMENTS

| | | | |
|---|---|---|---|
| 4,939,168 A | | 7/1990 | Gunasekera et al. |
| 5,010,099 A | | 4/1991 | Gunasekera et al. |
| 5,728,687 A | * | 3/1998 | Bissery ........................ 514/90 |
| 6,096,904 A | | 8/2000 | Smith, III et al. |

OTHER PUBLICATIONS

Chemical Abstract 128:10099, "The microtubule–stabilizing agent discodermolide . . . ", Kowalski et al (1997).*
Amadori et al., A phase I/II study of sequential doxorubicin and paclitaxel in the treatment of advanced breast cancer. Semin. Oncol., 23:16–22, 1996.
Balachandran et al., The potent microtubule–stabilizing agent (+)–discodermolide induces apoptosis in human breast carcinoma cells—preliminary comparisons to paclitaxel. Anti–Cancer Drugs, 9:67–76, 1998.
Balog et al., Total synthesis of (–)–epothilone A. Agnew. Chem. Int. Ed. Engl., 35:2801–03, 1996.
Bollag et al., Epothilones, a new class of microtubule–stabilizing agents with a Taxol–like mechanism of action. Cancer Res., 55:2325–33, 1995.
Cabral et al., Taxol–requiring mutant of Chinese hamster ovary cells with impaired mitotic spindle assembly. J. Cell Biol., 97:30–39, 1983.
Chen et al., The total synthesis of eleutherobin: a surprise ending. Agnew. Chem. Int. Ed., 37:789–92, 1998.
Felip et al., Superiority of sequential versus concurrent administration of paclitaxel with etoposide in advanced non–small cell lung cancer: comparison of two Phase II trials. Clin. Cancer Res., 4:2723–28, 1998.

Giannakakou et al., Combinations of paclitaxel and vinblastine and their effects on tubulin polymerization and cellular cytotoxicity: characterization of a synergistic schedule. Int. J. Cancer, 75:57–63, 1998.
Giannakakou et al., A beta–tubulin mutation confers epothilone resistance in human cancer cells. Proc. AACR, 40: 284, #1885, 1999.
Goldspiel, Clinical overview of the taxanes. Pharmacotherapy, 17:110S–125S, 1997.
Gottesman and Pastan, Biochemistry of multidrug resistance mediated by the multidrug transporter. Annu. Rev. Biochem., 62:385–427, 1993.
Haber et al., Altered expression of Mbeta2, the class II beta–tubulin isotype, in a murine J774.2 cell line with a high level of Taxol resistance. J. Biol. Chem., 270:31269–75, 1995.
Haux et al., The role of interleukin–2 in regulating the sensitivity of natural killer cells for Fas–mediated apoptosis. Cancer Immunol. Immunother., 48:139–46, 1999.
Hudes et al., Phase II trial of 96–hour paclitaxel plus oral estramustine phosphate in metastatic hormone–refractory prostate cancer. J. Clin. Oncol., 15: 3156–63, 1997.
Hung et al., (+)–Discodermolide binds to microtubules in stoichiometric ratio to tubulin dimers, blocks taxol binding and results in mitotic arrest. Chem. Biol., 3:287–93. 1996.
Jordan et al., Mechanism of mitotic block and inhibition of cell proliferation by taxol at low concentrations. Proc. Natl. Acad. Sci. USA, 90:9552–56, 1993.
Jordan et al., Mitotic block induced in HeLa cells by low concentrations of paclitaxel (Taxol) results in abnormal mitotic exit and apoptotic cell death. Cancer Res., 56:816–25, 1996.
Kavallaris et al., Taxol–resistant epithelial ovarian tumors are associated with altered expression of specific beta–tubulin isotypes. J. Clin. Invest., 100:1282–93, 1997.
Keren–Rosenberg and Muggia, Response to estramustine phosphate and paclitaxel in patients with advanced breast cancer: a phase I study. Semin. Oncol., 24:S3–26—S3–29, 1997.

(List continued on next page.)

Primary Examiner—Frederick Krass
(74) Attorney, Agent, or Firm—Amster, Rothstein & Ebenstein

(57) ABSTRACT

The present invention concerns an unexpected synergistic combination of known antineoplastic agents which provides unexpectedly greater efficacy than the single agents alone. Accordingly, the present invention provides a method of treating neoplasia in a subject in need of treatment, by administering to the subject an amount of paclitaxel effective to treat the neoplasia, in combination with an amount of discodermolide effective to treat the neoplasia, wherein a synergistic antineoplastic effect results. The present invention further provides a synergistic combination of antineoplastic agents, comprising an effective antineoplastic amount of paclitaxel and an effective antineoplastic amount of discodermolide.

11 Claims, 11 Drawing Sheets

OTHER PUBLICATIONS

Klaassen et al., Paclitaxel in combination with weekly 24–hour infusional 5–fluorouracil plus leucovorin in the second–line treatment of metastatic breast cancer: results of a phase II study. Ann. Oncol., 9:45–50, 1998.

Kowalski et al., Activities of the microtubule–stabilizing agents epothilones A and B with purified tubulin and in cells resistant to Paclitaxel (Taxol). J. Biol. Chem., 272:2534–41, 1997.

Kowalski et al., The microtubule–stabilizing agent discodermolide competitively inhibits the binding of Paclitaxel (Taxol) to tubulin polymers, enhances tubulin nucleation reactions more potently than Paclitaxel, and inhibits the growth of Paclitaxel–resistant cells. Mol. Pharmacol., 52:613–22, 1997.

Lindel et al., Eleutherobin, a new cytotoxin that mimics Paclitaxel (Taxol) by stabilizing microtubules. J. Am. Chem. Soc., 119:8744–45, 1997.

Long et al., Eleutherobin, a novel cytotoxic agent that induces tubulin polymerization, is similar to Paclitaxel (Taxol). Cancer Res., 58:1111–15, 1998.

Longley et al., Immunosuppression by discodermolide. Ann. NY Acad. Sci., 696:94–107, 1993.

Lowry et al., Protein measurement with the folin phenol reagent. J. Biol. Chem., 193:265–75, 1951.

Mann, Myxobacterial bounty. Nature, 385:117, 1997.

McDaid et al., Structure–activity profiles of eleutherobin analogs and their cross–resistance in Taxol–resistant cell lines. Cancer Chemother. Pharmacol., 44:131–37, 1999.

McDaid and Johnston, Synergistic interaction between paclitaxel and 8–chloro–adenosine 3', 5'–monophosphate in human ovarian carcinoma cell lines. Clin. Cancer Res., 5:215–20, 1999.

Meng et al., Total syntheses of epothilones A and B. J. Am. Chem. Soc., 119:10073–92, 1997.

Nerenberg et al., Total synthesis of the immunosuppressive agent (–)–discodermolide. J. Amer. Chem. Soc., 115:12, 621–22, 1993.

Ojima et al., A common pharmacophore for cytotoxic natural products that stabilize microtubules. Proc. Natl. Acad. Sci. USA, 96:4256–61, 1999.

Physicians' Desk Reference, 54th ed. (Montvale, NJ: Medical Economics Company, Inc.), 307, 682. 2000.

Rao et al., 3'–(p–azidobenzamido)taxol photolabels the N–terminal 31 amino acids of beta–tubulin. J. Biol. Chem., 269:3132–34, 1994.

Rao et al., Characterization of the taxol binding site on the microtubule. 2–(m–Azidobenzoyl) taxol photolabels a peptide (amino acids 217–231) of beta–tubulin. J. Biol. Chem., 270:20235–38, 1995.

Rowinsky et al., Sequences of taxol and cisplatin: a phase I and pharmacologic study. J. Clin. Oncol., 9:1692–1703, 1991.

Rowinsky and Donehower, Paclitaxel (Taxol). N. Engl. J. Med., 332:1004–14, 1995.

Schiff et al., Promotion of microtubule assembly in vitro by taxol. Nature, 277:665–67, 1979.

Schiff and Horwitz, Taxol stabilizes microtubules in mouse fibroblast cells. Proc. Natl. Acad. Sci. USA, 77:1561–65, 1980.

Su et al., Structure–activity relationships of the epothilones and the first in vivo comparison with Paclitaxel. Agnew. Chem. Int. Ed. Engl., 36:2093–96, 1997.

Su et al., Total synthesis of (–)–epothilone B: an extension of the Suzuki coupling method and insights into structure–activity relationships of the epothilones. Agnew. Chem. Int. Ed. Engl., 36:757–59, 1997.

Ter Haar et al., Discodermolide, a cytotoxic marine agent that stabilizes microtubules more potently than Taxol. Biochemistry, 35:243–50, 1996.

Torres and Horwitz, Mechanisms of Taxol–induced cell death are concentration dependent. Cancer Res., 58:3620–26, 1998.

Tortoriello et al., Phase I/II study of paclitaxel and vinorelbine in metastatic breast cancer. Breast Cancer Res. Treat., 47:91–97, 1998.

* cited by examiner

TAXOL   0   0.01   0.05   0.1   0.5   1   6   nM

TAXOL   0   0.01   0.05   0.1   0.5   2   6   12   nM

Mean CI=0.396 (*P*<0.0001)\*\*\*
Median CI=0.257 (*P*=0.0005)\*\*\*

Mean CI=0.476 (*P*=0.0002)\*\*\*
Median CI=0.297 (*P*=0.0008)\*\*\*

Mean CI=0.273 (*P*=0.0007)***
Median CI=0.252 (*P*<0.0001)***

Mean CI=1.18 (*P*=0.77)ns
Median CI=0.383 (*P*=0.0089)**

Mean CI=1.21 (*P*<0.0001)***
Median CI=1.12 (*P*=0.0005)***

Mean CI=1.534 (*P*=0.143)ns
Median CI=0.912 (*P*=0.468)ns

Mean CI=2.37 (*P*=0.045)*
Median CI=1.62 (*P*<0.0001)***

Mean CI=1.36 (*P*<0.0001)***
Median CI=1.31 (*P*<0.0001)***

METHOD FOR TREATING NEOPLASIA USING COMBINATION CHEMOTHERAPY

This application claims the benefit of U.S. Provisional application No. 60/233,191, filed Sep. 15, 2000.

STATEMENT OF GOVERNMENT INTEREST

This invention was made with government support under NIH Grant Nos. CA39821 and CA77263. As such, the United States government has certain rights in this invention.

BACKGROUND OF THE INVENTION

Neoplasia is a disease characterized by an abnormal proliferation of cell growth known as a neoplasm. Neoplasms may manifest in the form of a leukemia or a tumor, and may be benign or malignant. Malignant neoplasms, in particular, can result in a serious disease state, which may threaten life. Significant research efforts and resources have been directed toward the elucidation of antineoplastic measures, including chemotherapeutic agents, which are effective in treating patients suffering from neoplasia. Effective antineoplastic agents include those which inhibit or control the rapid proliferation of cells associated with neoplasms, those which effect regression or remission of neoplasms, and those which generally prolong the survival of patients suffering from neoplasia. Successful treatment of malignant neoplasia, or cancer, requires elimination of all malignant cells, whether they are found at the primary site, or whether they have extended to local-regional areas or have metastasized to other regions of the body. The major therapies for treating neoplasia are surgery and radiotherapy (for local and local-regional neoplasms) and chemotherapy (for systemic sites) [45].

The ideal antineoplastic drug would target and destroy only malignant neoplastic cells, without producing toxic or adverse effects on normal, nonmalignant cells. Malignant neoplastic cells usually have a shorter cell cycle than non-malignant cells. In contrast, most nonmalignant cells have a larger percentage of cells in the $G_0$ resting phase, resulting in a smaller proliferation fraction than that which is found in malignant cells. Accordingly, cellular kinetics are important in devising effective antineoplastic drug regimens. Many antineoplastic drugs are effective only if cells are in the cell cycle, and some drugs only work during a specific phase of the cell cycle. Cellular kinetics also may influence the dosage schedules and timing of treatment [45].

The failure of chemotherapeutic drugs in vivo, when efficacy has been documented in vitro, has led to extensive studies of drug resistance. One identified mechanism, pleiotropic resistance (or multidrug resistance), results from several genes that limit drug dwell and function in malignant neoplastic cells in the patient. Attempts to alter this resistance have not been successful. Thus, while single-drug chemotherapy has achieved cures in a limited number of cancers, regimens utilizing multiple drugs having different mechanisms of action, intracellular sites of activity, and toxicities (to reduce the potential compounding of toxicity) may provide significant cure rates [45].

Paclitaxel is a natural diterpene that has been isolated from several species of yew trees. It is also available commercially under the registered trademark Taxol [47]. Paclitaxel is an antimitotic agent (spindle poison) that enhances the assembly of microtubules from tubulin dimers, and stabilizes them against depolymerization [1, 47]. This stability results in the inhibition of normal dynamic reorganization of the microtubule network that is essential for vital interphase and mitotic cellular functions [47]. Paclitaxel is well-known as an effective antineoplastic chemotherapeutic agent. In fact, paclitaxel (Taxol) has been used with success in the treatment of leukemias and tumors, particularly breast, lung, and ovarian carcinomas [2], and malignant melanoma. Despite its considerable clinical success, there are a number of serious disadvantages to the use of paclitaxel. One problem, for example, is related to the extreme hydrophobic nature of the compound, which has made its formulation a continual problem. Paclitaxel also produces side-effects, including alopecia, arthralgia, myalgia, myelosuppression, and neuropathy [45]. Furthermore, the development of multidrug resistance in human tumors, as a result of overproduction of P-glycoprotein, may reduce the efficacy of paclitaxel in some patients.

The low aqueous solubility of paclitaxel and the development of clinical resistance to this antineoplastic agent have led to a search for new small-molecule compounds that may have an efficacy that is greater than, or comparable to, that of paclitaxel. Ideally, the new compounds would be more soluble in aqueous solvents, and would be poor substrates for P-glycoprotein—a known mediator of paclitaxel (Taxol) resistance [9]. The development of clinical resistance to paclitaxel also has highlighted the need for new combinations and schedules for these new antineoplastic agents. Indeed, while paclitaxel has had clinical success, both as a single agent and in combination with cisplatin [21], its use in combination with other antineoplastic agents is currently under intense evaluation, particularly for the treatment of advanced or recurrent cancers which are refractory to standard chemotherapy [22].

Classically, synergy is defined as the joint action of two or more drugs which produces a greater-than-additive therapeutic effect when compared to the therapeutic efficacy of each drug alone. Many combination therapies now being tested use drugs with dissimilar mechanisms of action, based on the rationale that targeting two independent pathways will result in enhanced cytotoxicity, whether additive or synergistic [23–26]. Nevertheless, one must not discount the use of agents with similar mechanisms of action or similar molecular targets [27–29].

Discodermolide is a natural lactone that has been isolated from the marine sponge, *Discodermia dissoluta*. Like paclitaxel, discodermolide is known to have activity against mammalian cancer cells. Discodermolide has a mechanism of action similar to that of paclitaxel: it has the ability to stabilize microtubules by binding to the same or overlapping sites on β-tubulin, thereby resulting in cell death and mitotic arrest [11]. Moreover, discodermolide has been predicted to be one hundred times more soluble than paclitaxel (Taxol), and to have a reduced affinity for P-glycoprotein [13].

SUMMARY OF THE INVENTION

The present invention is predicated on the surprising discovery that administration of Taxol in combination with discodermolide produces a synergistic antineoplastic effect. This discovery was unexpected, as the prior art suggested that combination chemotherapy using two drugs which bind to identical or overlapping sites on the same target generally results in additivity or antagonism. On the basis of this finding, the present invention provides a method of treating neoplasia in a subject in need of treatment, by administering to the subject an amount of paclitaxel effective to treat the neoplasia, in combination with an amount of discodermolide effective to treat the neoplasia, wherein a synergistic antineoplastic effect results.

Also provided by the present invention is a synergistic combination of antineoplastic agents, comprising an effective antineoplastic amount of paclitaxel and an effective antineoplastic amount of discodermolide.

Additional objects of the present invention will be apparent in view of the description which follows.

DETAILED DESCRIPTION OF THE INVENTION

Figure 1:
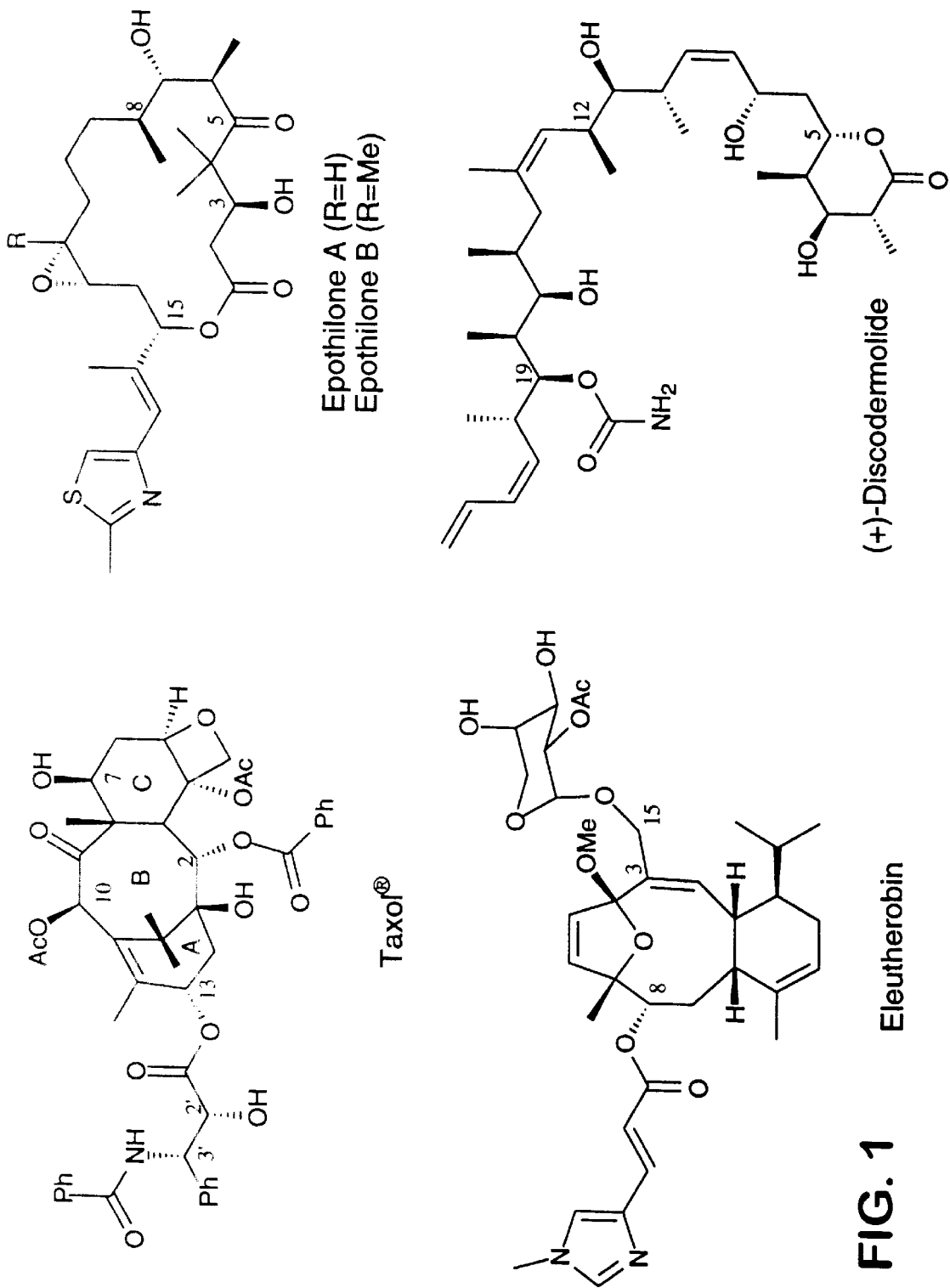
FIG. 1 depicts chemical structures of Taxol, epothilone A and B, eleutherobin, and discodermolide.

The present invention provides a method of treating neoplasia in a subject in need of treatment. As used herein, "neoplasia" refers to the uncontrolled and progressive multiplication of cells under conditions that would not elicit, or would cause cessation of, multiplication of normal cells. Neoplasia results in the formation of a "neoplasm", which is defined herein to mean any new and abnormal growth, particularly a new growth of tissue, in which the growth is uncontrolled and progressive. Malignant neoplasms are distinguished from benign in that the former show a greater degree of anaplasia, or loss of differentiation and orientation of cells, and have the properties of invasion and metastasis. Thus, neoplasia includes "cancer", which herein refers to a proliferation of cells having the unique trait of loss of normal controls, resulting in unregulated growth, lack of differentiation, local tissue invasion, and metastasis [45].

In the method of the present invention, neoplasia is treated in a subject in need of treatment by administering to the subject an amount of paclitaxel effective to treat the neoplasia, in combination with an amount of discodermolide effective to treat the neoplasia, wherein a synergistic antineoplastic effect results. The subject is preferably a mammal (e.g., humans, domestic animals, and commercial animals, including cows, dogs, monkeys, mice, pigs, and rats), and is most preferably a human.

As used herein, "paclitaxel" refers to paclitaxel and analogues and derivatives thereof, including, for example, a natural or synthetic functional variant of paclitaxel which has paclitaxel biological activity, as well as a fragment of paclitaxel having paclitaxel biological activity. As further used herein, the term "paclitaxel biological activity" refers to paclitaxel activity which interferes with cellular mitosis by affecting microtubule formation and/or action, thereby producing antimitotic and antineoplastic effects. Furthermore, as used herein, "antineoplastic" refers to the ability to inhibit or prevent the development or spread of a neoplasm, and to limit, suspend, terminate, or otherwise control the maturation and proliferation of cells in a neoplasm.

Additionally, as used herein, "discodermolide" refers to discodermolide and analogues and derivatives thereof, including, for example, a natural or synthetic functional variant of discodermolide which has discodermolide biological activity, as well as a fragment of discodermolide having discodermolide biological activity. As further used herein, the term "discodermolide biological activity" refers to discodermolide activity which has the ability to stabilize microtubules by binding to β-tubulin, thereby resulting in cell death and mitotic arrest and producing antimitotic and antineoplastic effects. Paclitaxel and discodermolide, and their analogues and derivatives, are referred to herein as "antineoplastic agents".

Methods of preparing paclitaxel and its analogues and derivatives are well-known in the art, and are described, for example, in U.S. Pat. Nos. 5,569,729; 5,565,478; 5,530,020; 5,527,924; 5,484,809; 5,475,120; 5,440,057; and 5,296,506. Paclitaxel and its analogues and derivatives are also available commercially. Synthetic paclitaxel, for example, can be obtained from Bristol-Myers Squibb Company, Oncology Division (Princeton, N.J.), under the registered trademark Taxol. Taxol for injection may be obtained in a single-dose vial, having a concentration of 30 mg/5 mL (6 mg/mL per 5 mL) [47]. Taxol and its analogues and derivatives have been used successfully to treat leukemias and tumors. In particular, Taxol is useful in the treatment of breast, lung, and ovarian cancers. Discodermolide and its analogues and derivatives can be isolated from extracts of the marine sponge, *Discodermia dissoluta*, as described, for example, in U.S. Pat. Nos. 5,010,099 and 4,939,168. Discodermolide and its analogues and derivatives also may be synthesized, as described, for example, in U.S. Pat. No. 6,096,904. Moreover, both paclitaxel and discodermolide may be synthesized in accordance with known organic chemistry procedures [46] that are readily understood by one skilled in the art.

In the method of the present invention, an amount of paclitaxel or discodermolide that is "effective to treat the neoplasia" is an amount that is effective to ameliorate or minimize the clinical impairment or symptoms of the neoplasia, in either a single or multiple dose. For example, the clinical impairment or symptoms of the neoplasia may be ameliorated or minimized by diminishing any pain or discomfort suffered by the subject; by extending the survival of the subject beyond that which would otherwise be expected in the absence of such treatment; by inhibiting or preventing the development or spread of the neoplasm; or by limiting, suspending, terminating, or otherwise controlling the maturation and proliferation of cells in the neoplasm. For example, doses of paclitaxel (Taxol) administered intraperitoneally may be between 1 and 10 mg/kg, and doses administered intravenously may be between 1 and 3 mg/kg, or between 135 mg/m² and 200 mg/m². However, the amounts of paclitaxel and discodermolide effective to treat neoplasia in a subject in need of treatment will vary depending on the particular factors of each case, including the type of neoplasm, the stage of neoplasia, the subject's weight, the severity of the subject's condition, and the method of administration. These amounts can be readily determined by the skilled artisan.

The method of the present invention may be used to treat neoplasia in a subject in need of treatment. Neoplasias for which the present invention will be particularly useful include, without limitation, carcinomas, particularly those of the bladder, breast, cervix, colon, head, kidney, lung, neck, ovary, prostate, and stomach; lymphocytic leukemias, particularly acute lymphoblastic leukemia and chronic lymphocytic leukemia; myeloid leukemias, particularly acute monocytic leukemia, acute promyelocytic leukemia, and chronic myelocytic leukemia; malignant lymphomas, particularly Burkitt's lymphoma and Non-Hodgkin's lymphoma; malignant melanomas; myeloproliferative diseases; sarcomas, particularly Ewing's sarcoma, hemangiosarcoma, Kaposi's sarcoma, liposarcoma, peripheral neuroepithelioma, and synovial sarcoma; and mixed types of neoplasias, particularly carcinosarcoma and Hodgkin's disease [45]. Preferably, the method of the present invention is used to treat breast cancer, colon cancer, leukemia, lung cancer, malignant melanoma, ovarian cancer, or prostate cancer.

In the method of the present invention, paclitaxel is administered to a subject in combination with discodermolide, such that a synergistic antineoplastic effect is produced. A "synergistic antineoplastic effect" refers to a greater-than-additive antineoplastic effect which is produced by a combination of two drugs, and which exceeds that which would otherwise result from individual administration of either drug alone. Administration of paclitaxel in combination with discodermolide unexpectedly results in a synergistic antineoplastic effect by providing greater efficacy than would result from use of either of the antineoplastic agents alone. Discodermolide enhances paclitaxel's effects. Therefore, lower doses of one or both of the antineoplastic agents may be used in treating neoplasias, resulting in increased therapeutic efficacy and decreased side-effects.

Discodermolide also may provide a means to circumvent clinical resistance due to overproduction of P-glycoprotein. Accordingly, the combination of paclitaxel and discodermolide may be advantageous for use in subjects who exhibit resistance to paclitaxel (Taxol). Since Taxol is frequently utilized in the treatment of human cancers, a strategy to enhance its utility in the clinical setting, by combining its administration with that of discodermolide, may be of great benefit to many subjects suffering from malignant neoplasias, particularly advanced cancers.

One measure of synergy between two drugs is the combination index (CI) method of Chou and Talalay [37], which is based on the median-effect principle. This method calculates the degree of synergy, additivity, or antagonism between two drugs at various levels of cytotoxicity. Where the CI value is less than 1, there is synergy between the two drugs. Where the CI value is 1, there is an additive effect, but no synergistic effect. CI values greater than 1 indicate antagonism. The smaller the CI value, the greater the synergistic effect. Another measurement of synergy is the fractional inhibitory concentration (FIC) [48]. This fractional value is determined by expressing the $IC_{50}$ of a drug acting in combination, as a function of the $IC_{50}$ of the drug acting alone. For two interacting drugs, the sum of the FIC value for each drug represents the measure of synergistic interaction. Where the FIC is less than 1, there is synergy between the two drugs. An FIC value of 1 indicates an additive effect. The smaller the FIC value, the greater the synergistic interaction. In the method of the present invention, combination therapy using paclitaxel and discodermolide preferably results in an antineoplastic effect that is greater than additive, as determined by any of the measures of synergy known in the art.

In the method of the present invention, administration of paclitaxel "in combination with" discodermolide refers to co-administration of the two antineoplastic agents. Co-administration may occur concurrently, sequentially, or alternately. Concurrent co-administration refers to administration of both paclitaxel and discodermolide at essentially the same time. For concurrent co-administration, the courses of treatment with paclitaxel and with discodermolide may be run simultaneously. For example, a single, combined formulation, containing both an amount of paclitaxel and an amount of discodermolide in physical association with one another, may be administered to the subject. The single, combined formulation may consist of an oral formulation, containing amounts of both paclitaxel and discodermolide, which may be orally administered to the subject, or a liquid mixture, containing amounts of both paclitaxel and discodermolide, which may be injected into the subject.

It is also within the confines of the present invention that an amount of paclitaxel and an amount of discodermolide may be administered concurrently to a subject, in separate, individual formulations. Accordingly, the method of the present invention is not limited to concurrent co-administration of paclitaxel and discodermolide in physical association with one another.

In the method of the present invention, paclitaxel and discodermolide also may be co-administered to a subject in separate, individual formulations that are spaced out over a period of time, so as to obtain the maximum efficacy of the combination. Administration of each drug may range in duration from a brief, rapid administration to a continuous perfusion. When spaced out over a period of time, co-administration of paclitaxel and discodermolide may be sequential or alternate. For sequential co-administration, one of the antineoplastic agents is separately administered, followed by the other. For example, a full course of treatment with paclitaxel may be completed, and then may be followed by a full course of treatment with discodermolide. Alternatively, for sequential co-administration, a full course of treatment with discodermolide may be completed, then followed by a full course of treatment with paclitaxel. For alternate co-administration, partial courses of treatment with paclitaxel may be alternated with partial courses of treatment with discodermolide, until a full treatment of each drug has been administered.

The antineoplastic agents of the present invention (i.e., paclitaxel and discodermolide, either in separate, individual formulations, or in a single, combined formulation) may be administered to a human or animal subject by known procedures, including, but not limited to, oral administration, parenteral administration (e.g., intramuscular, intraperitoneal, intravascular, intravenous, or subcutaneous administration), and transdermal administration. Preferably, the antineoplastic agents of the present invention are administered orally or intravenously.

For oral administration, the formulations of paclitaxel and discodermolide (whether individual or combined) may be presented as capsules, tablets, powders, granules, or as a suspension. The formulations may have conventional additives, such as lactose, mannitol, corn starch, or potato starch. The formulations also may be presented with binders, such as crystalline cellulose, cellulose derivatives, acacia, corn starch, or gelatins. Additionally, the formulations may be presented with disintegrators, such as corn starch, potato starch, or sodium carboxymethyl-cellulose. The formulations also may be presented with dibasic calcium phosphate anhydrous or sodium starch glycolate. Finally, the formulations may be presented with lubricants, such as talc or magnesium stearate.

For parenteral administration, the formulations of paclitaxel and discodermolide (whether individual or combined) may be combined with a sterile aqueous solution which is preferably isotonic with the blood of the subject. Such formulations may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be presented in unit or multi-dose containers, such as sealed ampules or vials. Moreover, the formulations may be delivered by any mode of injection, including, without limitation, epifascial, intracapsular, intracutaneous, intramuscular, intraorbital, intraperitoneal (particularly in the case of localized regional therapies), intraspinal, intrasternal, intravascular, intravenous, parenchymatous, or subcutaneous.

For transdermal administration, the formulations of paclitaxel and discodermolide (whether individual or combined) may be combined with skin penetration enhancers, such as propylene glycol, polyethylene glycol, isopropanol, ethanol, oleic acid, N-methylpyrrolidone, and the like, which increase the permeability of the skin to the antineoplastic agent, and permit the antineoplastic agent to penetrate through the skin and into the bloodstream. The antineoplastic agent/enhancer compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in a solvent such as methylene chloride, evaporated to the desired viscosity, and then applied to backing material to provide a patch.

It is within the confines of the present invention that the formulations of paclitaxel and discodermolide (whether individual or combined) may be further associated with a pharmaceutically-acceptable carrier, thereby comprising a pharmaceutical composition. The pharmaceutically-acceptable carrier must be "acceptable" in the sense of being compatible with the other ingredients of the composition, and not deleterious to the recipient thereof. Examples of acceptable pharmaceutical carriers include Cremophor™ (a common vehicle for Taxol), as well as carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may conveniently be presented in unit dosage.

The formulations of the present invention may be prepared by methods well-known in the pharmaceutical art. For example, the active compound may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the antineoplastic agents of the present invention (i.e., paclitaxel and discodermolide, and their analogues and derivatives, either in separate, individual formulations, or in a single, combined formulation) to a subject to treat neoplasia. The antineoplastic agents are provided in amounts that are effective to treat neoplasia in the subject. These amounts may be readily determined by the skilled artisan.

It is also within the confines of the present invention that paclitaxel and discodermolide be co-administered in combination with radiation therapy or an antiangiogenic compound (either natural or synthetic). Examples of antiangiogenic compounds with which paclitaxel and discodermolide may be combined include, without limitation, angiostatin, tamoxifen, thalidomide, and thrombospondin.

The present invention further provides a synergistic combination of antineoplastic agents. As defined above, "antineoplastic" refers to the ability to inhibit or prevent the development or spread of a neoplasm, and to limit, suspend, terminate, or otherwise control the maturation and proliferation of cells in a neoplasm. As used herein, a "synergistic combination of antineoplastic agents" refers to a combination of antineoplastic agents that achieves a greater antineoplastic effect than would otherwise result if the antineoplastic agents were administered individually. Additionally, as described above, the "antineoplastic agents" of the present invention are paclitaxel and discodermolide, and their analogues and derivatives, either in separate, individual formulations, or in a single, combined formulation. Administration of paclitaxel in combination with discodermolide unexpectedly results in a synergistic antineoplastic effect by providing greater efficacy than would result from use of either of the antineoplastic agents alone.

In the synergistic combination of the present invention, paclitaxel and discodermolide may be combined in a single formulation, such that the amount of paclitaxel is in physical association with the amount of discodermolide. This single, combined formulation may consist of an oral formulation, containing amounts of both paclitaxel and discodermolide, which may be orally administered to the subject, or a liquid mixture, containing amounts of both paclitaxel and discodermolide, which may be injected into the subject.

Alternatively, in the synergistic combination of the present invention, a separate, individual formulation of paclitaxel may be combined with a separate, individual formulation of discodermolide. For example, an amount of paclitaxel may be packaged in a vial or unit dose, and an amount of discodermolide may be packaged in a separate vial or unit dose. A synergistic combination of paclitaxel and discodermolide then may be produced by mixing the contents of the separate vials or unit doses in vitro. Additionally, a synergistic combination of paclitaxel and discodermolide may be produced in vivo by co-administering to a subject the contents of the separate vials or unit doses, according to the methods described above. Accordingly, the synergistic combination of the present invention is not limited to a combination in which amounts of paclitaxel and discodermolide are in physical association with one another in a single formulation.

The synergistic combination of the present invention comprises an effective antineoplastic amount of paclitaxel and an effective antineoplastic amount of discodermolide. As used herein, an "effective antineoplastic amount" of paclitaxel or discodermolide is an amount of paclitaxel or discodermolide that is effective to ameliorate or minimize the clinical impairment or symptoms of neoplasia in a subject, in either a single or multiple dose. For example, the clinical impairment or symptoms of neoplasia may be ameliorated or minimized by diminishing any pain or discomfort suffered by the subject; by extending the survival of the subject beyond that which would otherwise be expected in the absence of such treatment; by inhibiting or preventing the development or spread of the neoplasm; or by limiting, suspending, terminating, or otherwise controlling the maturation and proliferation of cells in the neoplasm.

The effective antineoplastic amounts of paclitaxel and discodermolide will vary depending on the particular factors of each case, including the type of neoplasm, the stage of neoplasia, the subject's weight, the severity of the subject's condition, and the method of administration. For example, effective antineoplastic amounts of paclitaxel (Taxol) administered intraperitoneally may range from 1 to 10 mg/kg, and doses administered intravenously may range from 1 to 3 mg/kg, or from 135 mg/m$^2$ to 200 mg/m$^2$. Nevertheless, the appropriate effective antineoplastic amounts of paclitaxel and discodermolide can be readily determined by the skilled artisan.

The synergistic combination described herein may be useful for treating neoplasia in a subject in need of treatment. Paclitaxel and discodermolide, which comprise the synergistic combination of the present invention, may be co-administered to a subject concurrently, sequentially, or alternately, as described above. Moreover, the paclitaxel and discodermolide of the present invention may be administered to a subject by any of the methods, and in any of the formulations, described above.

The present invention is described in the following Experimental Details section, which is set forth to aid in the understanding of the invention, and should not be construed to limit in any way the scope of the invention as defined in the claims which follow thereafter.

Experimental Details

1. Introduction

Taxol is an antimitotic agent that enhances the assembly of microtubules, and stabilizes them against depolymerization [1]. The cellular target of Taxol is the microtubule, specifically the β-tubulin subunit in the polymer [3, 4]. Incubation of cells with Taxol causes the formation of stable bundles or parallel arrays of microtubules, resulting in the arrest of cells in mitosis [5]. Low concentrations of Taxol (10 nM) induce a mitotic block without microtubule-bundle formation, and initiate apoptosis in HeLa cells [6, 7]. These observations have led to the concept that Taxol can cause cell death by different mechanisms, depending on the drug concentration [8].

The low aqueous solubility of Taxol and the development of clinical drug resistance have led to a search for new compounds that may have an efficacy that is greater than, or comparable to, that of Taxol. Ideally, the new agents would be more soluble in aqueous solvents, and would be poor substrates for P-glycoprotein—a known mediator of Taxol-resistance [9].

Several promising antimicrotubule drugs with unique structures unrelated to the structure of Taxol have been reported to have mechanisms of action similar to that of Taxol (FIG. 1). Discodermolide, for example, was isolated from a marine sponge. It was reported to induce the assembly of microtubules in vitro more rapidly than Taxol, and to cause mitotic arrest and microtubule bundling [10–12]. Discodermolide has been predicted to be 100 times more soluble than Taxol, and to have a reduced affinity for P-glycoprotein [13]. Epothilones A and B, isolated from a Myxobacterium fermentation broth, also were found to induce tubulin polymerization, to arrest cells in mitosis, and to cause the formation of microtubule bundles [14, 15]. Epothilone B was reported to be more potent than Taxol and epothilone A in promoting microtubule assembly in vitro [15]. The epothilones are 30 times more water-soluble than Taxol [16].

Structure-activity studies with the epothilones have demonstrated that the acyl region (C1–C8) is essential for Taxol-like activity [17]. In addition, studies have shown that the epothilones retain sensitivity in P-glycoprotein-expressing cells that are resistant to Taxol [15]. Recently, a fourth microtubule-stabilizing agent, eleutherobin, was isolated from a marine soft coral, and was shown to have activity comparable to that of Taxol [18]. Structure-activity analyses of eleutherobin analogues concluded that the C8 urocanic acid moiety is required for Taxol-like activity [19]. Eleutherobin displayed cross-resistance in MDR cell lines—an effect that was reversible by verapamil—thereby suggesting that eleutherobin is a substrate of P-glycoprotein [19, 20]. While there is no clinical data available to date on the therapeutic activity of these new antimitotic agents, their distinct chemical structures and improved aqueous solubility will influence their therapeutic activity based on the pharmacokinetics, bioavailability, and metabolism of each drug.

Classically, synergy is defined as the joint action of two or more drugs which produces greater-than-additive therapeutic effect when compared to the therapeutic efficacy of each drug alone. Many combination therapies now being tested use drugs with dissimilar mechanisms of action, based on the rationale that targeting two independent pathways will result in enhanced cytotoxicity, whether additive or synergistic [23–26]. Nevertheless, one must not discount the use of agents with similar mechanisms of action or molecular targets [27–29]. Although Taxol has had clinical success, both as a single agent and in combination with cisplatin [21], its use in combination with other antitumor agents is currently under intense evaluation, particularly for the treatment of advanced or recurrent cancers which are refractory to standard chemotherapy [22]. The development of clinical drug resistance has highlighted the need for new chemotherapeutic drugs, as well as new combinations and schedules for these agents.

The present experiment examined the effects on a Taxol-resistant human non-small-cell lung carcinoma cell line, A549-T12, of the three new classes of antimicrotubule agents. Although isolated as a Taxol-resistant cell line, it later was found that the A549-T12 cell line requires low concentrations of Taxol (2–6 nM) for normal growth. The mechanism of resistance/dependence has not yet been determined; however, it is known that these cells do not express P-glycoprotein, and do have alterations in their β-tubulin isotype expression [30]. The primary objectives of this experiment were to compare and contrast the cytotoxic profiles of these three new classes of antimitotic agents in Taxol-sensitive and Taxol-resistant cell lines, and to investigate their ability to substitute for Taxol in the A549-T12 cell line. The results obtained led to an extensive evaluation of the interaction between Taxol and discodermolide in four human cancer cell lines, using the combination index (CI) method.

2. Materials and Methods

A. Antimitotic agents

Taxol was obtained from the Drug Development Branch of the National Cancer Institute (Bethesda, Md.). Epothilones A and B and eleutherobin were synthesized as described [31–34]. Discodermolide was synthesized as described below. All drugs were dissolved in sterile DMSO and stored at −20° C.

B. Cell cultures

The drug-sensitive mouse macrophage-like cell line, J774.2, and its Taxol-resistant cell line, J7-T3-1.6, were maintained as previously described [35]. J7-T3-1.6 cells were grown in the presence of 1.6 $\mu$M Taxol. Drug-sensitive and vinblastine-resistant human ovarian carcinoma cell lines, SKOV3 and SKVLB, were obtained from Dr. V. Ling, and were maintained as previously described [19]. Both J7-T3-1.6 and SKVLB cells overexpress P-glycoprotein. SKVLB cells were grown in the presence of 1 $\mu$M vinblastine. The Taxol-resistant human non-small-cell lung carcinoma cell line, A549-T12, was derived from the drug-sensitive A549 cell line; both cell lines were maintained as previously described [30]. The A549-T12 cell line was grown in the presence of 12 nM Taxol. The human breast carcinoma cell lines, MCF-7 and MDA-MB-231, were both maintained in IMEM medium containing 10% heat-inactivated FBS and 1% P/S.

C. Cytotoxicity assays

For the A549 cell lines, cells were seeded at a density of $1 \times 10^4$ cells/mL (A549) or $3 \times 10^4$ cells/mL (A549-T12), in triplicate, 6-well plates, and allowed to attach for 24 h. After incubation with varying drug concentrations for 72 h (FIG. 3), adherent cells were trypsinized and counted (Coulter counter model ZF0031, Coulter Corp., Miami, Fla.), and the $IC_{50}$ was determined. The SKOV3 and SKVLB cell lines were assayed in a similar manner. Cells were seeded in triplicate, at a density of $6 \times 10^3$ cells/mL (SKOV3) or $12 \times 10^3$ cells/mL (SKVLB), in 6-well plates, and incubated with a drug for 6 days. An accurate $IC_{50}$ only could be derived after a 6-day incubation period, due to the high resistance of these cell lines. J774.2 and J7-T3-1.6 cells were plated at a density of $2 \times 10^4$ cells/well, in 96-well plates, and allowed to attach overnight. Serial dilutions of each drug were performed, and the cells were incubated for 72 h. The $IC_{50}$ was determined using the CellTiter 96™ AQ$_{ueous}$ nonradioactive cell proliferation assay (Promega, Madison, Wis.), which correlates with the number of live cells. Different methods for determining $IC_{50}$ values were used, depending on the most accurate method for each particular set of cell lines.

For the drug combination assay, A549-T12 cells were seeded in triplicate, at a density of $4 \times 10^4$ cells/mL, in 96-well plates, in the absence of Taxol or in the presence of various concentrations of Taxol, in combination with serial dilutions of each test drug. After a 72-h incubation, the plates were assayed using the colorimetric proliferation assay. In order to sustain the growth of A549-T12 cells in the absence of Taxol, cells were seeded at the higher densities described above.

D. Methylene blue assay

Figure 2:
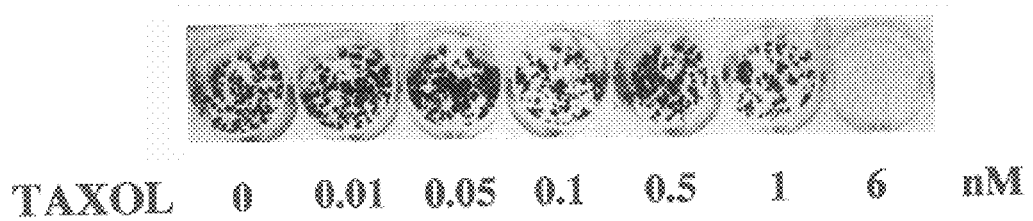
FIG. 2 illustrates that A549-T12 cells require Taxol for normal growth. A549 and A549-T12 cells were grown in the absence or presence of various concentrations of Taxol for 8 to 11 days. The cells were then stained with methylene blue, as described below.
Figure 2:
Figure 3A:
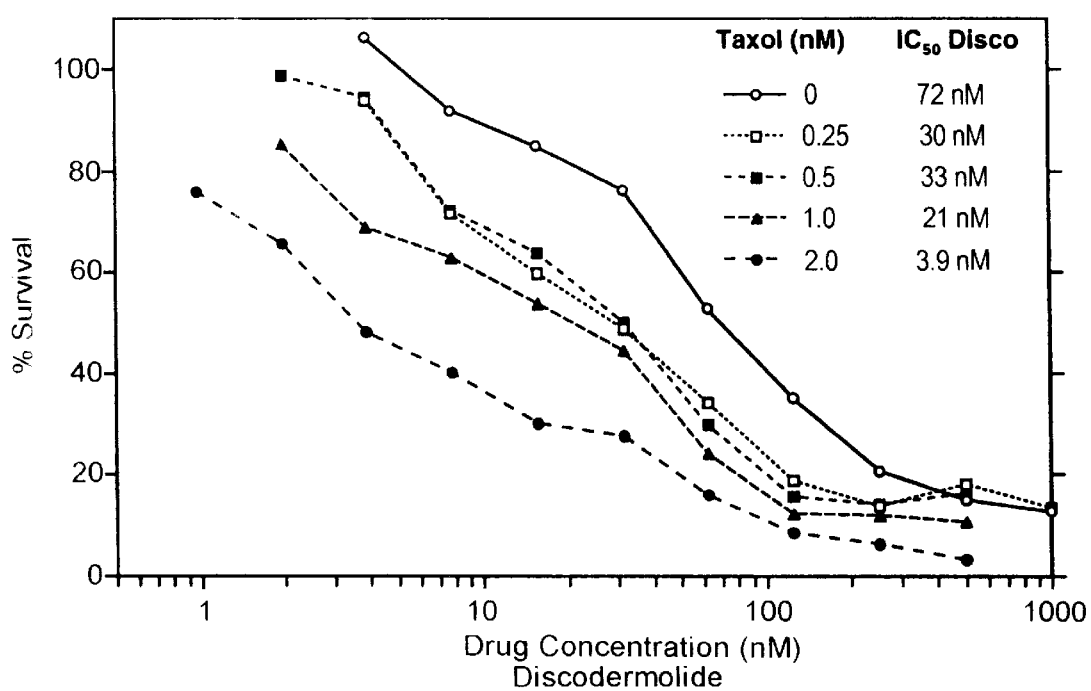
FIG. 3 demonstrates that discodermolide requires Taxol to inhibit effectively A549-T12 cell proliferation. For the drug combination assay, the cells were analyzed after 72 h using a cell proliferation assay, as described below. A: cytotoxicity curves of A549-T12 cells in the absence of Taxol or in the presence of Taxol (in various concentrations), in combination with a range of discodermolide concentrations; B–D: cytotoxicity curves of A549-T12 cells in the absence or presence of 2 nM Taxol, in combination with eleutherobin or the epothilones. —0—: no Taxol; ---●---: 2 nM Taxol.
Figure 3B:
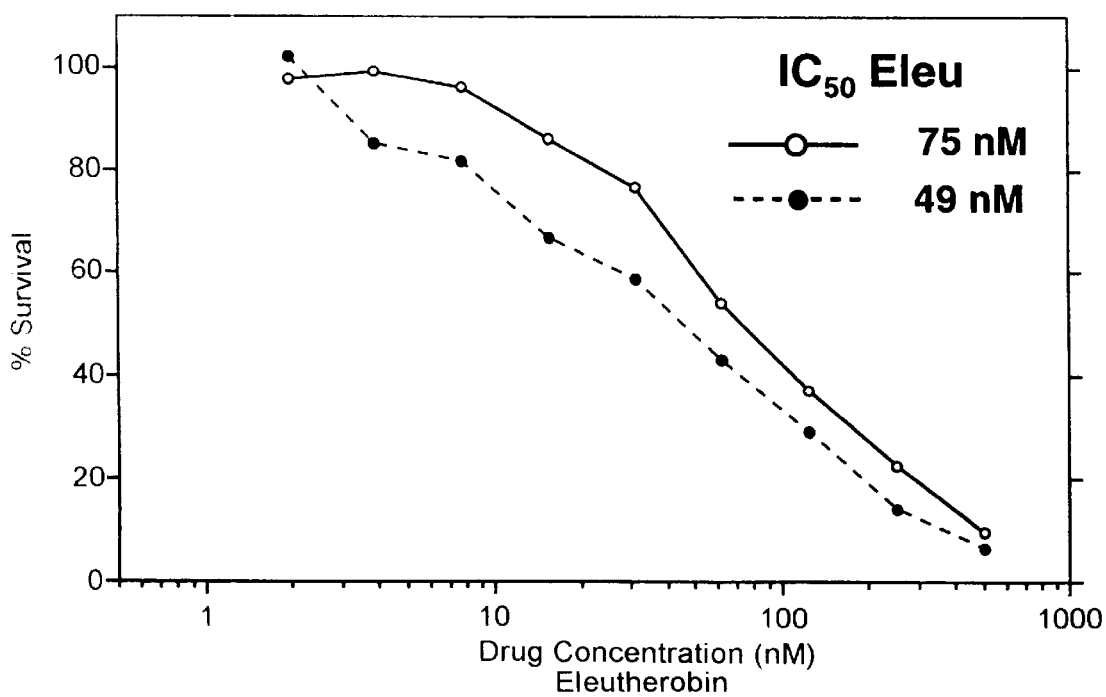
Figure 3C:
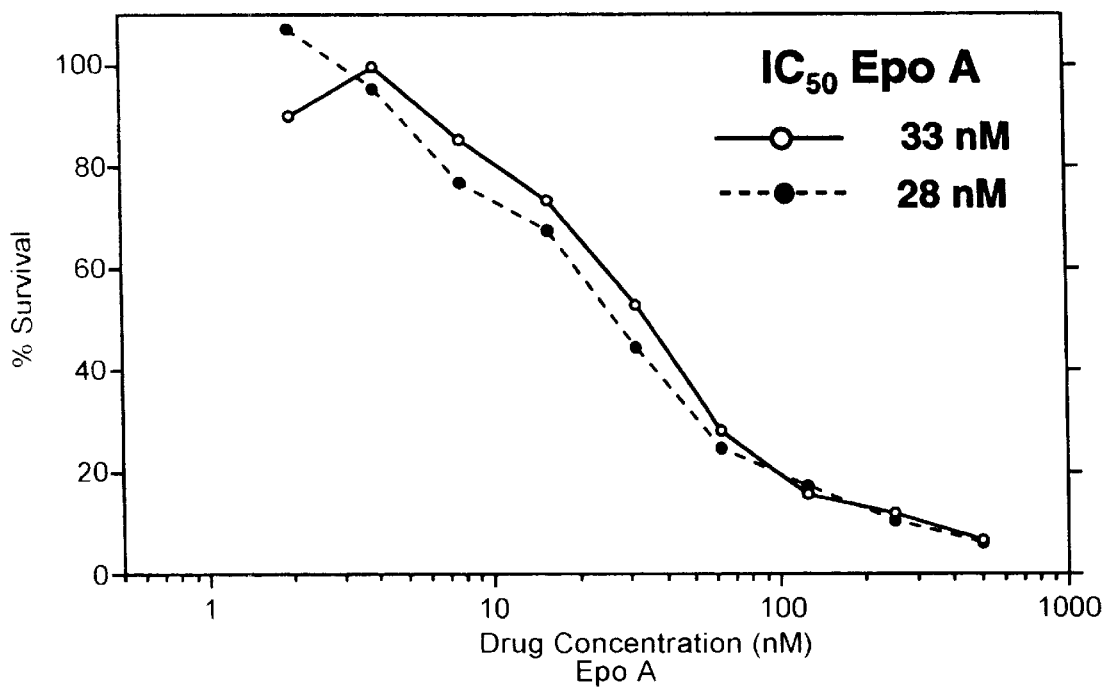
Figure 3D:
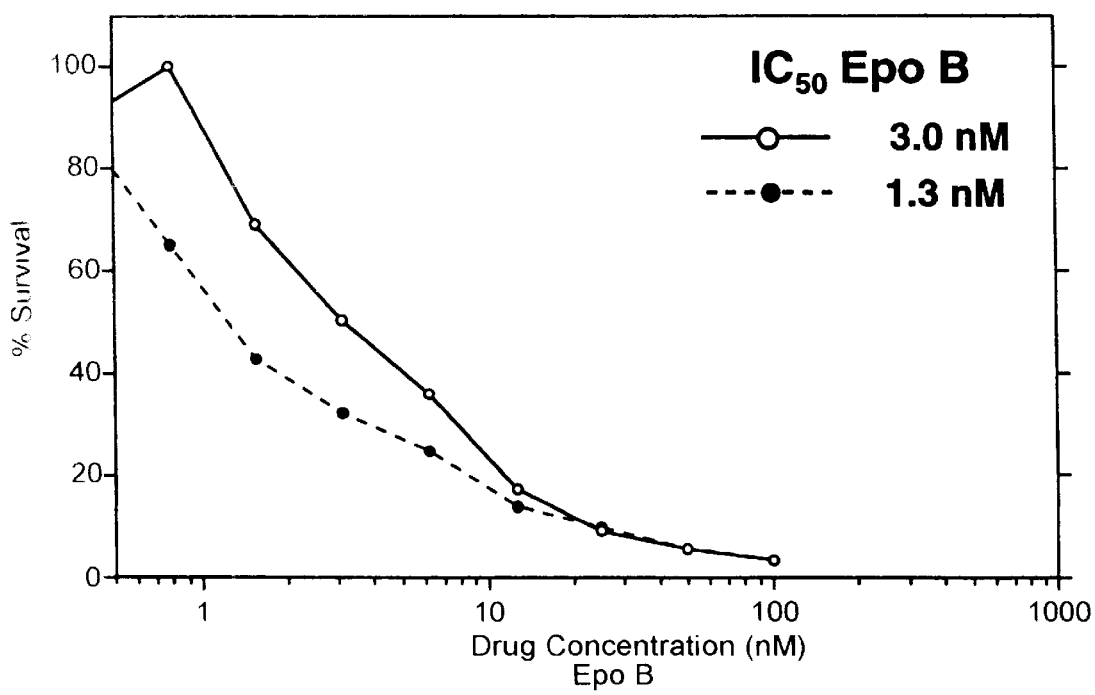

Cells were seeded in 24-well plates at a density of 400 cells/well (A549) or 500 cells/well (A549-T12), and treated with different concentrations of Taxol. Following 8 to 11 days of growth, the medium was removed, and cells were stained with 0.5% methylene blue (Sigma) in 50% ethanol for 20 min, then rinsed with distilled water (FIG. 2).

E. Indirect immunofluorescence

A549-T12 cells, which were grown to subconfluency on glass cover slips in the absence of drug or in the presence of different drugs at varying concentrations (FIG. 4), were prepared for immunofluorescence microscopy as previously described [8], with the following modifications: (a) nonspecific binding was blocked using 10% normal goat serum in PBS for 30 min at 37° C.; (b) cells were incubated with a monoclonal antibody to α-tubulin (Sigma; 1:100 dilution; 5% normal goat serum in PBS), followed by a Cy3-conjugated anti-mouse IgG secondary antibody (Amersham, Arlington Heights, Ill.; 1:1000 dilution); and (c) slides were analyzed using the Zeiss Axioskop microscope (rhodamine filter) at 63× magnification.

F. Flow cytometry

For the drug substitution experiments, A549-T12 cells were seeded at a density of $3 \times 10^4$ cells/mL in 75-cm$^2$ flasks, and treated with various drugs at the indicated concentrations (FIG. 5). After 48 h, both adherent and nonadherent cells were harvested, fixed in 70% ethanol for at least 20 min, permeabilized with 0.1% Triton X-100 in PBS for 3 min, and stained for 30 min at 37° C. with 10 $\mu$g/mL of propidium iodide (Sigma) in a PBS solution containing 1 $\mu$g/mL of RNase A (Boehringer Mannheim, Indianapolis, Ind.). Cell-cycle analysis was performed using the Becton Dickinson FACScan and the CellQuest program. For the drug combination studies, A549 cells were seeded at a density of $3 \times 10^4$ cells/mL in 75-cm$^2$ flasks, and grown in the presence of Taxol, discodermolide, or both, at their equipotent ratios of 1:5 respectively, for 24 h (FIG. 6). The cells then were prepared as described above.

G. Multiple-drug-effect analysis

Cells were seeded in triplicate in either 96-well or 24-well plates. Following adherence, the different drugs were added (alone or in combination) for 72 h (96 h for MDA-MB-231) (FIG. 7). Ten-fold serial dilutions were performed for both the single drugs and the combinations, in order to obtain good dosage ranges. The doses which were evaluated were all based on the $IC_{50}$ values of each individual drug, and combined drug regimens were evaluated at their equipotent ratios, i.e., equivalent to the ratio of their $IC_{50}$ values. Dose-response curves were determined from cell survival data obtained using the colorimetric cell proliferation assay (Promega) or cell counts. The combination index method of Chou and Talalay [37] was used to analyze the nature of the interaction between Taxol and discodermolide or epothilone B, using the Calcusyn software (Biosoft, Cambridge, UK).

In summary, the interaction of the two drugs was quantified by determining a combination index (CI) at various levels of cytotoxicity or cell kill. CI values of less than or greater than 1 indicate synergism or antagonism, respectively, while a value of 1 indicates additivity. The CI values were calculated using both the mutually-nonexclusive assumption (dissimilar mechanism of action of both drugs) and the mutually-exclusive assumption (similar mechanism of action). Each datum point represents the mean (±SE) of at least three independent experiments, each performed in triplicate. One-sample t-tests and Wilcoxon signed rank tests (two-tailed) were used to determine whether the means and medians, respectively, of the CI values were significantly different from 1.

3. Results

A. Cytotoxicity of antimitotic agents in both P-glycoprotein- and non-P-glycoprotein-expressing cell lines The mouse macrophage-like cell line, J774.2, was most sensitive to epothilone B, but quite insensitive to eleutherobin (Table 1). The J7-T3-1.6 cell line, which was selected with Taxol and which overexpresses P-glycoprotein, displayed significant cross-resistance to vinblastine, and low resistance to epothilone A, epothilone B, and discodermolide. Due to the insensitivity to eleutherobin of J7-T3-1.6 cells, it was not possible to determine accurately its cross-resistance in this cell line. A human ovarian carcinoma cell line, SKOV3, displayed the highest sensitivity to epothilone B and vinblastine, with decreased but similar responses to Taxol, epothilone A, discodermolide, and eleutherobin. The resistance pattern for the vinblastine-resistant SKVLB cells, which also overexpress P-glycoprotein, indicated low-level cross-resistance to epothilone A, epothilone B, and discodermolide. However, definite cross-resistance to eleutherobin was exhibited. Experiments examining the steady-state accumulation of [$^3$H]Taxol indicated that eleutherobin, in contrast to the epothilones and discodermolide, was a substrate for P-glycoprotein (data not shown).

In contrast to Taxol-resistant cells that overexpress P-glycoprotein, the A549-T12 cell line does not express P-glycoprotein, and is 9-fold resistant to Taxol. This cell line has a requirement for low levels of Taxol (2–6 nM) for normal growth. In contrast, the growth of the parental A549 cell line was unaffected by subnanomolar concentrations of Taxol (FIG. 2). At 6 nM, Taxol was cytotoxic in A549 cells; however, A549-T12 cells grew normally in 6 nM Taxol. Epothilone A, eleutherobin, and discodermolide displayed comparable activities in A549 cells, while epothilone B was more potent (Table 2). The A549-T12 cell line exhibited cross-resistance to epothilone A, epothilone B, and eleutherobin, but no cross-resistance to discodermolide, vinblastine, or colchicine. In the absence of 2 nM Taxol, A549-T12 cells were 20-fold less sensitive to discodermolide (FIG. 3). When Taxol was titrated with a range of discodermolide concentrations, the potency of discodermolide was maximal in the presence of 2 nM Taxol (FIG. 3). For Taxol concentrations above 2 nM, the combination of discodermolide and Taxol became significantly cytotoxic. Of the drugs evaluated in the present experiment, this effect was seen only with the combination of Taxol and discodermolide.

Figure 4A:
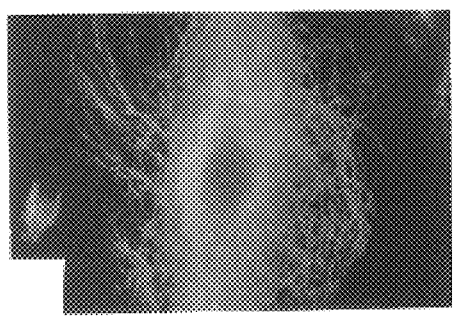
FIG. 4 illustrates that A549-T12 cells display a normal microtubule cytoskeleton in the presence of the epothilones and eleutherobin. A549-T12 cells were grown on cover slips and treated with the different compounds for 48 h. Cells were then permeabilized, fixed, and incubated with an α-tubulin antibody, as described below. A: 2 nM Taxol; B: 2 nM epothilone A; C: 0.1 nM epothilone B; D: 18 nM eleutherobin; E: no drug; F: 2 nM discodermolide; G: 12 nM discodermolide; H: 2 nM vinblastine.
Figure 4E:
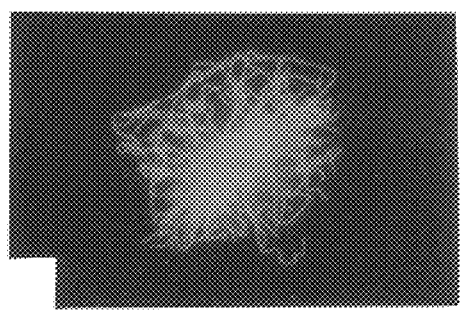
Figure 4B:
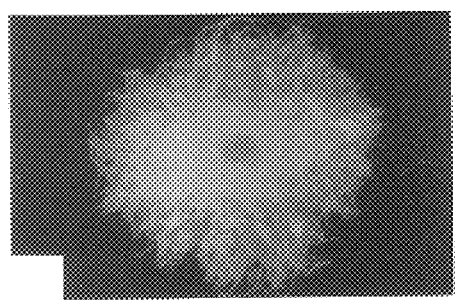
Figure 4F:
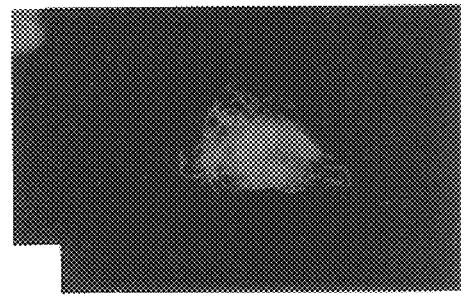
Figure 4C:
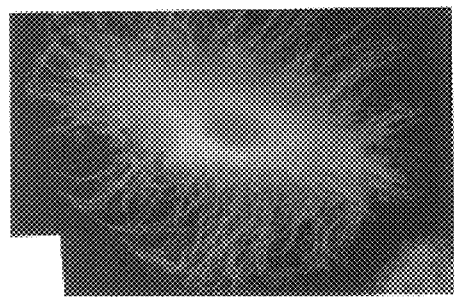
Figure 4G:
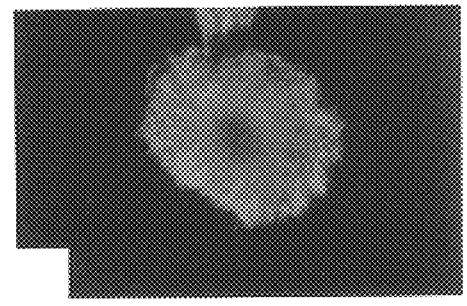
Figure 4D:
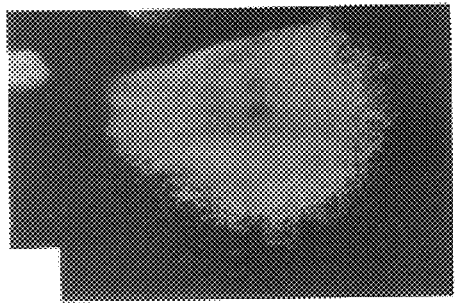
Figure 4H:
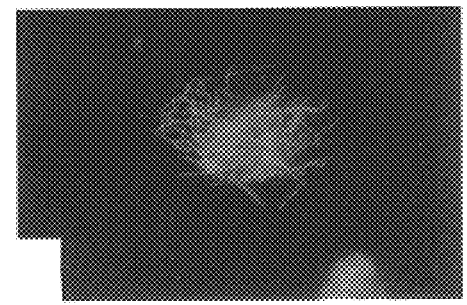

B. The A549-T12 cell line displays a normal microtubule cytoskeleton in the presence of the epothilones and eleutherobin When A549-T12 cells were grown in the absence of Taxol for 48 h, the microtubule cytoskeleton appeared diminished when examined by immunofluorescence (FIG. 4E). In contrast, A549-T12 cells exhibited a normal microtubule cytoskeleton in the presence of Taxol, epothilone A, epothilone B, and eleutherobin (FIGS. 4A–D), thereby indicating that the epothilones and eleutherobin were able to replace Taxol in this cell line. The different concentrations of the various drugs which were used reflect their distinct cytotoxic potencies. Neither discodermolide nor vinblastine was able to substitute for Taxol in A549-T12 cells (FIGS. 4F and 4H). At higher concentrations of discodermolide ($\geq 12$ nM), the microtubules became arranged in bundle-like formations at the periphery of the cell (FIG. 4G); this effect was not observed with higher doses of the other drugs tested (data not shown).

TABLE 1

Cytotoxicity of antimitotic agents in drug-resistant cell lines that overexpress P-glycoprotein

| Cell Lines | $IC_{50}$ (nM)[a] | | | | | |
|---|---|---|---|---|---|---|
| | Taxol | VBL | EpoA | EpoB | Disco | Eleu |
| J774.2 | 67 ± 7.0[b] | 6.0 ± 2.7 | 10.6 ± 2.0 | 0.4 ± 0.1 | 36 ± 5.5 | 394.2 ± 5.8 |
| J7-T3-1.6 | 18,000 ± 2645 | 767 ± 351 | 170 ± 14 | 12 ± 4.0 | 1,050 ± 70 | >5,000 |
| Fold resistance[c] | 268.7 | 127.8 | 16 | 30 | 29.2 | >12.7 |
| SKOV3 | 2.0 ± 0.1 | 1.1 ± 0.1 | 10.3 ± 4.5 | 0.5 ± 0.09 | 9.7 ± 0.3 | 8.2 ± 3.8 |
| SKVLB | 13,333 ± 1,154 | 1,880.3 ± 347.5 | 190 ± 14 | 9.5 ± 2.1 | 575 ± 233 | >5000 |
| Fold resistance[d] | 6,666.5 | 1,709.4 | 18.5 | 19.0 | 59.3 | >609.8 |

[a]$IC_{50}$ = drug concentration that inhibits cell division by 50% after 72 h (J774.2 and J7-T3-1.6) or 6 days (SKOV3 and SKVLB)

[b]Mean ± SE

[c]Ratio of $IC_{50}$ for resistant cell line (J7-T3-1.6) to that for sensitive cell line (J774.2) after 72 h

[d]Ratio of $IC_{50}$ for resistant cell line (SKOV3) to that for sensitive cell line (SKVLB) after 6 days VBL = vinblastine; EpoA = epothilone A; EpoB = epothilone B; Disco = discodermolide; Eleu = eleutherobin

TABLE 2

Cytotoxicity of antimitotic agents in a Taxol-resistant cell line that does not express P-glycoprotein

| Cell Lines | IC$_{50}$ (nM)[a] | | | | | | |
|---|---|---|---|---|---|---|---|
|  | Taxol | EpoA | EpoB | Eleu | Disco | VBL | CLC |
| A549 | 2 ± 0.14[b] | 6.4 ± 2.0 | 0.7 ± 0.1 | 14 ± 2.8 | 8.1 ± 0.14 | 1.8 + 0.21 | 33 + 10.6 |
| A549-T12[c] | 18.7 ± 0.9 | 34 ± 3.1 | 3.3 ± 0.72 | 69 ± 11.3 | 6.5 ± 2.4 | 1.8 ± 0.18 | 33 ± 12.7 |
| Fold resistance[d] | 9.4 | 5.3 | 4.7 | 4.9 | 0.8 | 1.0 | 1.0 |

Figure 5A:
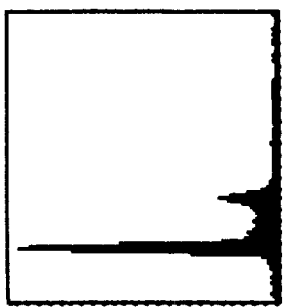
FIG. 5 demonstrates that the epothilones and eleutherobin, but not discodermolide, can substitute for Taxol in the A549-T12 Taxol-requiring cell line. Cells were incubated with the different agents for 48 h, fixed, stained with propidium iodide, and analyzed by flow cytometry, as described below. A: 2 nM Taxol; B: 2 nM epothilone A; C: 0.5 nM epothilone B; D: 18 nM eleutherobin; E: no drug; F: 2 nM discodermolide; G: 6 nM discodermolide; H: 12 nM discodermolide.
Figure 5B:
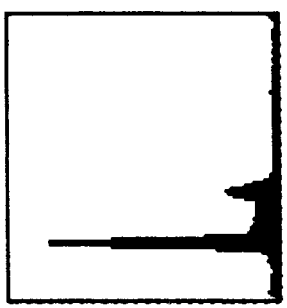
Figure 5C:
Figure 5D:
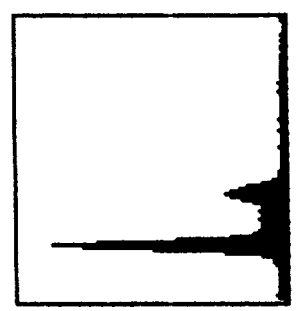
Figure 5E:
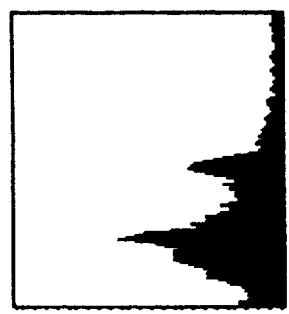
Figure 5F:
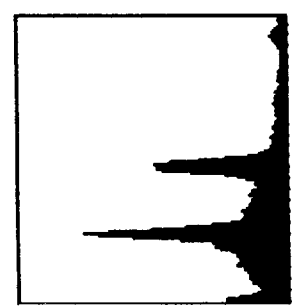
Figure 5G:
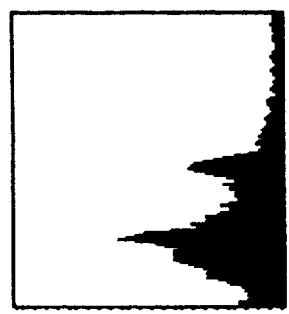
Figure 5H:
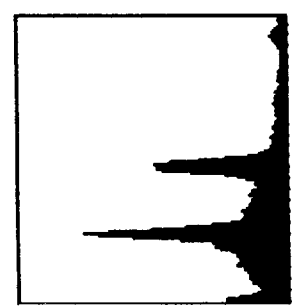
Figure 6A:
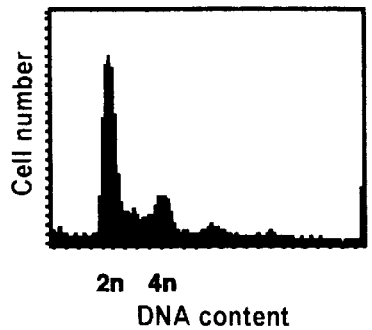
FIG. 6 illustrates that concurrent Taxol and discodermolide exposure caused an increase in the hypodiploid fraction of A549 cells. Cells were incubated for 24 h with Taxol, discodermolide, or a combination, then fixed, stained with propidium iodide, and analyzed by flow cytometry, as described below. A: 0.1 nM Taxol; B: 1 nM Taxol; C: 5 nM Taxol; D: 0.5 nM discodermolide; E: 5 nM discodermolide; F: 25 nM discodermolide; G: 0.1 nM Taxol+0.5 nM discodermolide; H: 1 nM Taxol+5 nM discodermolide; I: 5 nM Taxol+25 nM discodermolide.
Figure 6B:
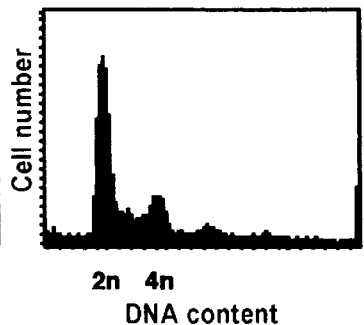
Figure 6C:
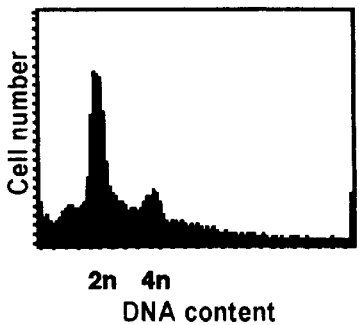
Figure 6D:
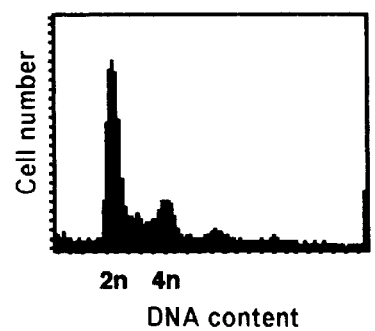
Figure 6E:
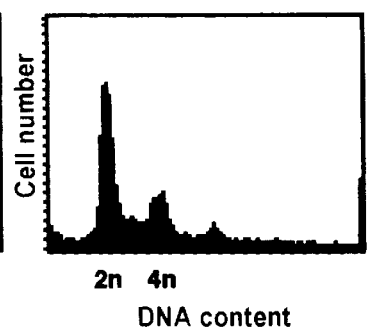
Figure 6F:
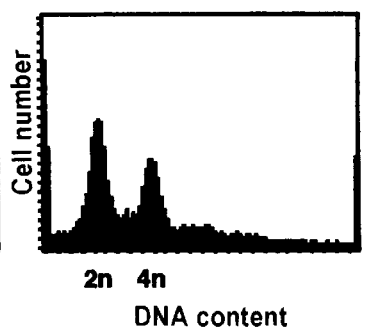
Figure 6G:
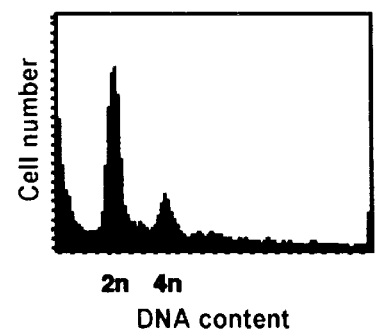
Figure 6H:
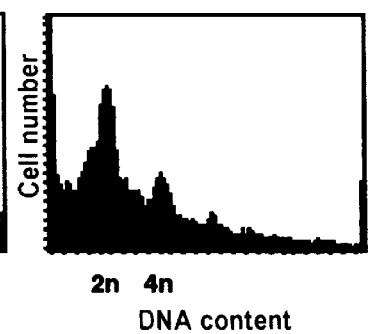
Figure 6I:
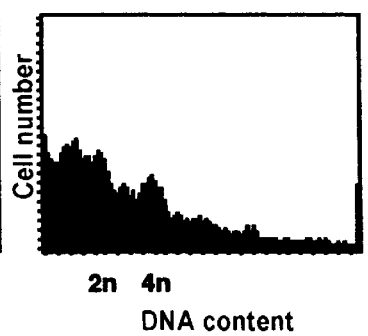
Figure 7A:
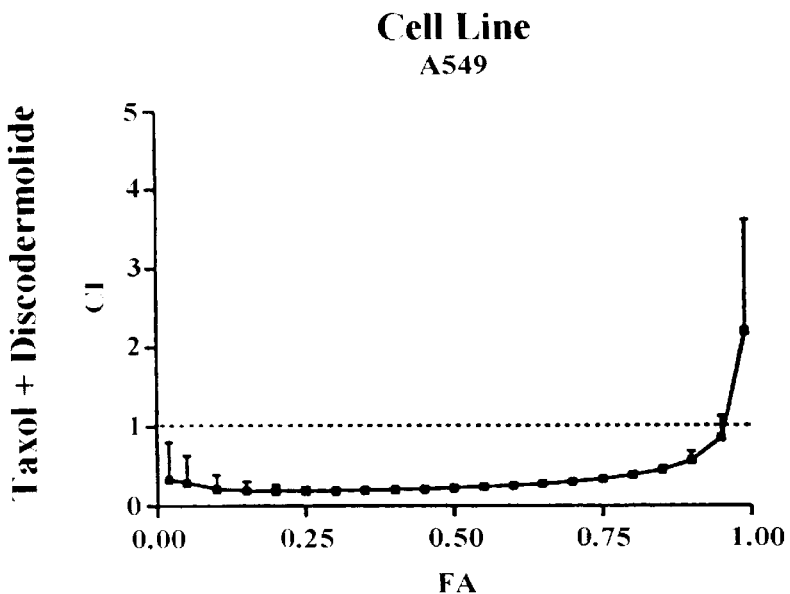
FIG. 7 demonstrates that Taxol and discodermolide act synergistically in various human cancer cell lines. Cells were incubated with the different drug combinations for 72 h (A549, SKOV3, MCF-7) or 96 h (MDA-MB-231), and assayed, as described below. The combination index (CI) as a function of fraction affected (FA) was plotted for the concurrent combination of Taxol and discodermolide, or Taxol and epothilone B, in human cancer cell lines at their equipotent ratios. Data points represent mean CI values (based on the mutually-nonexclusive assumption) ±SE from at least three independent experiments. P values indicate the level of significance of mean and median CI values compared to CI=1.
Figure 7B:
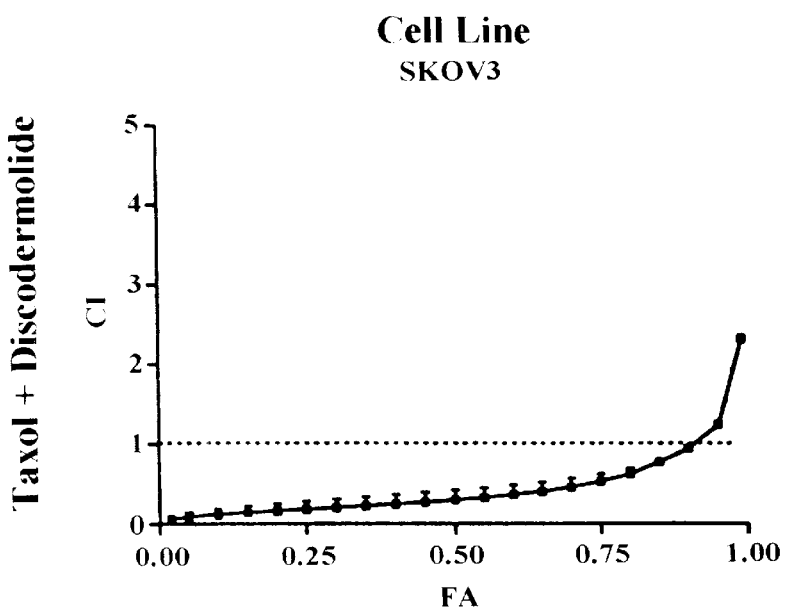
Figure 7C:
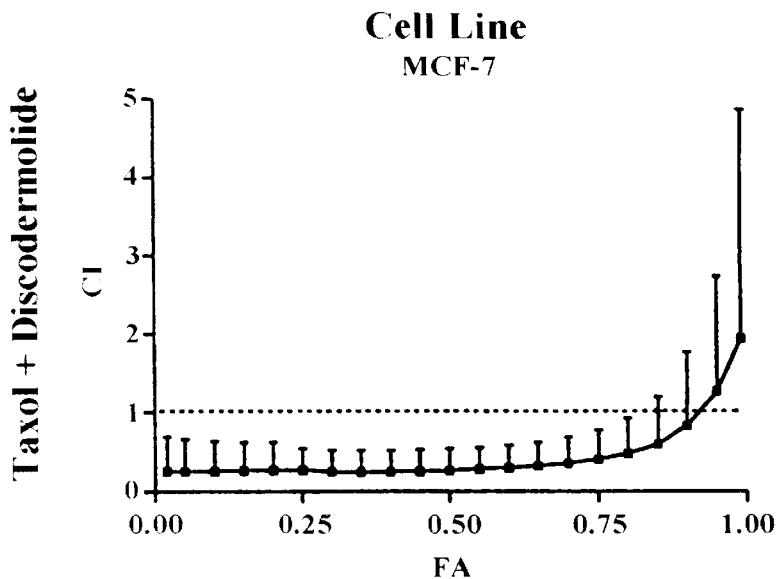
Figure 7D:
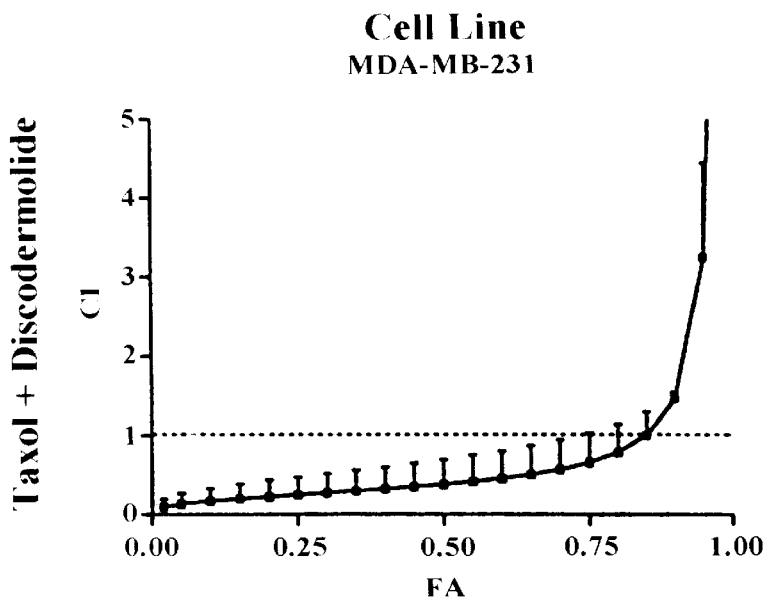
Figure 7E:
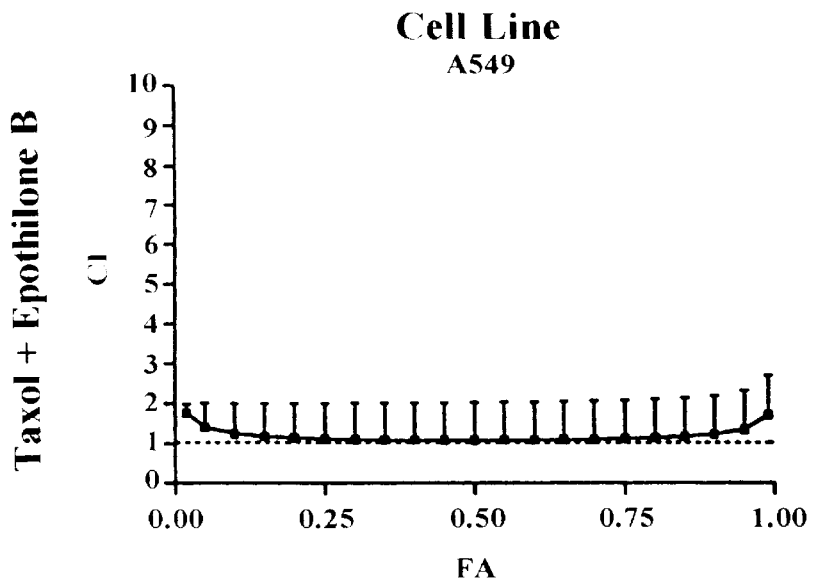
Figure 7F:
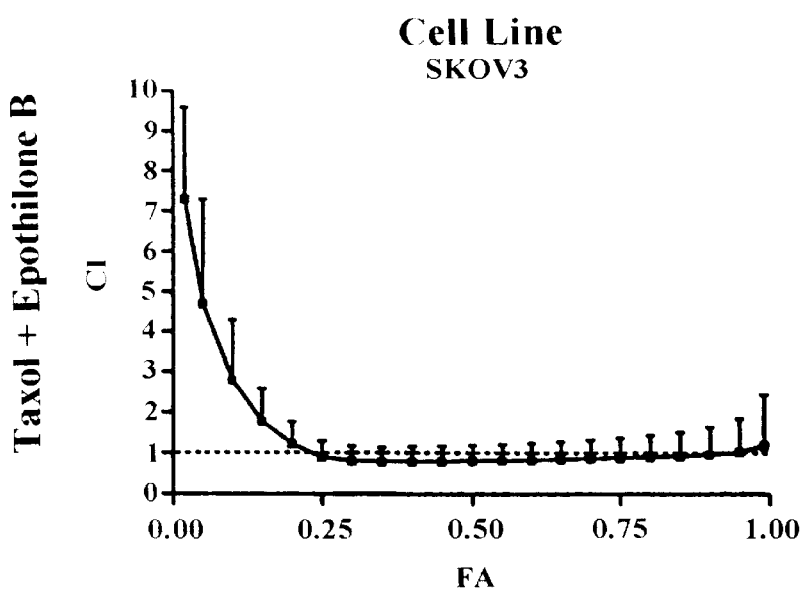
Figure 7G:
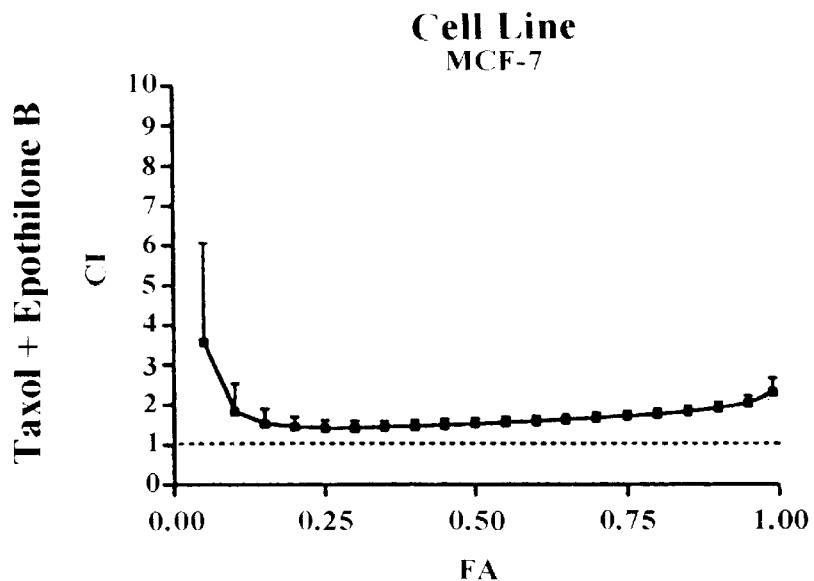
Figure 7H:
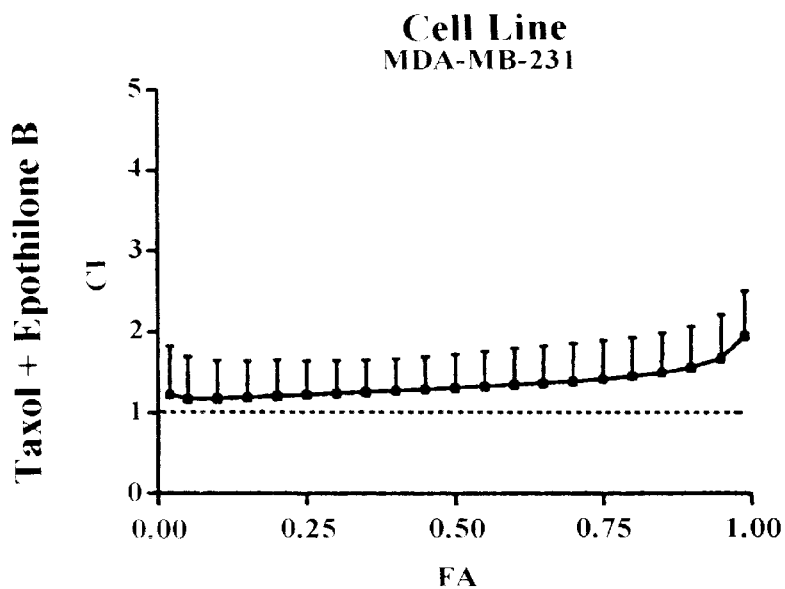

[a]IC$_{50}$ = drug concentration that inhibits cell division by 50% after 72 h
[b]Mean ± SE
[c]Cells were maintained in 2 nM Taxol during cross-resistance experiments
[d]Ratio of IC$_{50}$ for A549-T12 resistant cell line to that for A549 sensitive cell line
EpoA = epothilone A; EpoB = epothilone B; Eleu = eleutherobin; Disco = discodermolide; VBL = vinblastine; CLC = colchicine C. The epothilones and eleutherobin can substitute for taxol in the taxol-dependent cell line, and can reverse the mitotic block caused by taxol removal Cell-cycle analysis by flow cytometry revealed a normal cell-cycle profile for A549-T12 resistant cells in the presence of 2 nM Taxol (FIG. 5A). When Taxol was removed, the resistant cells became blocked at the G$_2$-M-phase transition (FIG. 5E). In the presence of epothilone A, epothilone B, or eleutherobin, the A549-T12 cells also exhibited a normal cell-cycle profile (FIGS. 5B–5D). In contrast, the addition of discodermolide (2 or 6 nM) did not prevent the development of a G$_2$-M-phase block in the resistant cell line (FIGS. 5F and 5G). These data corroborate the immunofluorescence results, and further show that discodermolide is unable to substitute for Taxol in A549-T12 cells. At lower concentrations of discodermolide (0.001–1.0 nM), the cells also displayed a G$_2$-M-phase block. At higher concentrations of discodermolide (12–24 nM), there was a substantial increase in the hypodiploid population, resulting in loss of the cell-cycle profile (FIG. 5H). A549-T12 cells also demonstrated a mitotic block in the presence of vinblastine (data not shown).

Flow cytometry was used to investigate whether the sustained G$_2$-M -phase block induced by Taxol removal could be reversed in the presence of the epothilones, eleutherobin, and discodermolide (data not shown). A549-T12 cells were grown in the absence of Taxol for 48 h, then incubated with various concentrations of Taxol, epothilone A, epothilone B, and eleutherobin for 48 h, which resulted in the return of a normal cell-cycle profile. There also was an increase in the hypodiploid population after reversal of the G$_2$-M-phase block. The mitotic block in the Taxol-dependent cells was irreversible in the presence of vinblastine or a range of discodermolide concentrations (0.001–24.0 nM).

D. Taxol and discodermolide are a synergistic drug combination in various human carcinoma cell lines To extend the observation made in A549-T12 cells that the cytotoxicity of discodermolide was potentiated in the presence of Taxol (FIG. 3), and to fully evaluate the nature of the interaction of Taxol with discodermolide, the inventors analyzed the combination of both drugs using flow cytometry and multiple-drug-effect analysis. Flow cytometric analysis revealed an increase in the hypodiploid population of A549 drug-sensitive cells when concurrently exposed to nanomolar concentrations of Taxol and discodermolide (up to 5 nM Taxol and 25 nM discodermolide) (FIG. 6). At these concentrations, there was no subsequent rise in the number of cells in the G$_2$-M phase of the cell cycle. Only at high concentrations of both Taxol and discodermolide (10 nM Taxol and 50 nM discodermolide) was there a concomitant increase in the number of cells in the mitotic phase (data not shown).

Multiple-drug-effect analysis utilized the method of Chou and Talalay [37], which resolves the degree of synergy, additivity, or antagonism at various levels of cell kill. For these experiments, the interaction of Taxol with epothilone B was used as a positive control to verify that other microtubule-stabilizing agents did not have the same interaction with Taxol as did discodermolide. FIG. 7 summarizes the multiple-drug-effect analysis of four human cancer cell lines, represented as fractional cell growth inhibition (FA) as a function of the combination index (CI). Since it could not be determined whether the interactions between the various classes of microtubule-binding agents were mutually exclusive or nonexclusive, the CI values were routinely calculated using both methods. This gave almost identical results in all experiments.

The data presented herein summarize the CI values based on the more conservative assumption of mutual nonexclusion. CI values for the combination of concurrent Taxol and discodermolide were significantly less than 1 in all four cell lines, indicating a synergistic drug interaction. In all cell lines tested, this interaction was effective over a 3- to 4-fold log concentration of either drug. The inventors also evaluated the effects of sequential drug exposure, in which either Taxol or discodermolide was administered alone for 24 h before administration of the second drug. Sequencing of the drugs also resulted in the same magnitude of synergism as concurrent exposure, and was independent of drug schedule (data not shown). Conversely, additive interactions were observed in all four cell lines following concurrent exposure to both Taxol and epothilone B, indicating that the synergism observed between Taxol and discodermolide was not shared by other microtubule-polymerizing agents.

4. Discussion

Taxol has proved to be one of the most interesting antitumor agents of the past decade. In addition to its clinical activity in a variety of human malignancies, its mechanism of action (which includes stabilization of microtubules, formation of parallel arrays of microtubules, and activation of a number of signal-transduction pathways) has encouraged scientists to continue investigation of this drug. In spite of its considerable clinical success, there are serious problems with Taxol. One problem, for example, is related to the extreme hydrophobic nature of the compound, which has made its formulation a continual problem. A second problem is the development of drug resistance in human tumors, which relates to the overproduction of P-glycoprotein. Based on the success of Taxol in the clinical setting, there has been an ongoing search for new small molecules with Taxol-like activity.

During the past few years, new natural products from diverse sources, and having distinct chemical structures, have emerged. Despite this structural diversity, a model has been proposed that depicts a common pharmacophore linking these agents [38]. The epothilones, eleutherobin, and discodermolide all have mechanisms of action bearing definite similarities to that of Taxol. In the inventors' in vitro microtubule polymerization assay, Taxol, the epothilones, eleutherobin, and discodermolide all enhanced the assembly of stable microtubules in the absence of GTP, which is usually required for normal in vitro microtubule assembly.

Here, the inventors disclose a comprehensive analysis of the cross-resistant profiles of the epothilones, eleutherobin, and discodermolide in Taxol-sensitive and Taxol-resistant cell lines, which have different mechanisms of resistance. The data indicate little, if any, cross-resistance of the epothilones and discodermolide in Taxol-resistant cell lines that overproduce P-glycoprotein. These data are consistent with results obtained from the Taxol accumulation experiment in a Taxol-resistant murine cell line in which the epothilones and discodermolide were unable to reverse the reduction in Taxol accumulation, reinforcing the finding that they are not substrates for P-glycoprotein.

The present experiment has taken advantage of an interesting cell line, A549-T12, which was isolated in the inventors' laboratory as a Taxol-resistant cell line, and which is maintained in 12 nM Taxol. A549-T12 cells have approximately 9-fold resistance to Taxol, and do not overproduce P-glycoprotein. On further examination, it was observed that the cells grew poorly, if at all, in the absence of Taxol. The inventors disclose that, after 48 h in the absence of Taxol, the microtubule cytoskeleton of A549-T12 cells is diminished, and the cells undergo a mitotic block; however, addition of Taxol after 48 h reverses these abnormalities. It appears that the cells have modified their normal biochemistry to survive in the presence of the drug to such an extent that they have become dependent on the drug for normal growth. A possible mechanism for this phenomenon may be the selection of a variant form of tubulin having microtubules that are normally unstable, but which thrive in the presence of low concentrations of Taxol. Taxol-requiring Chinese hamster ovary cell lines have been described previously [39].

The availability of the A549-T12 cell line has allowed the inventors to distinguish discodermolide from the other antimitotic compounds described herein. The epothilones and eleutherobin demonstrated cross-resistance in A549-T12 cells, and could substitute for Taxol, reversing the $G_2$-M-phase block which is induced after Taxol withdrawal. This contrasts with what was observed with discodermolide, which did not exhibit cross-resistance, and was unable to substitute for Taxol. In fact, it is clear that, in A549-T12 cells, low concentrations of Taxol are required for discodermolide to exert its maximum cytotoxic effects, thereby suggesting that the cellular substrate for discodermolide is a microtubule having a conformation that has been modified by Taxol. A previous report has alluded to the requirement of an intact microtubule cytoskeleton for discodermolide binding to occur in cells [11]. Vinblastine, like Taxol, is an antimitotic agent which also has, as a cellular target, the tubulin/microtubule system. In contrast to Taxol, its major binding site is the tubulin dimer, and, in vitro, the drug promotes microtubule depolymerization [40]. Although vinblastine is an excellent substrate for P-glycoprotein, and the inventors observed high cross-resistance in the cell lines overproducing P-glycoprotein, there is no cross-resistance in the A549-T12 cell line. The data concerning cross-resistance with the various antimitotic agents in A549-T12 cells are intriguing, and require a thorough understanding of the mechanisms of resistance and dependence in the A549-T12 cell line.

Median-effect analysis using the combination index (CI) method of Chou and Talalay [37] confirmed a synergistic interaction between Taxol and discodermolide. In contrast, the combination of discodermolide and epothilone B was additive, indicating that there is a specific relationship between Taxol and discodermolide resulting in synergistic cytotoxicity. The inventors also have shown that low concentrations of Taxol and discodermolide caused an increase in the hypodiploid population of cells without a corresponding increase in the $G_2$-M-phase cell population. Therefore, the inventors speculate that the synergism observed between Taxol and discodermolide is probably due to the potentiation of apoptosis by this drug combination, although the precise mechanism remains to be determined.

Previous work has shown a schedule-dependent synergistic interaction between Taxol and vinblastine, both of which bind to separate distinct targets on the tubulin macromolecule [41]. Here, the inventors describe synergy between Taxol and discodermolide, two drugs which apparently bind to the same or overlapping sites on β-tubulin [11]. It is uncommon for two drugs which bind to identical sites on the same target to synergize when administered concurrently or in sequence. More often, this type of drug combination results in additivity (similar to what was observed with Taxol and epothilone B) or antagonism, since both drugs cannot bind the same site simultaneously. In A549-T12 cells, discodermolide does not exhibit cross-resistance, unlike the epothilones and eleutherobin. Furthermore, it has been reported that epothilone A-resistant ovarian carcinoma cells that do not express P-glycoprotein exhibit cross-resistance to Taxol, baccatin, and taxotere, but do not exhibit cross-resistance to discodermolide [42]. Taken together, these findings imply that the Taxol and discodermolide binding sites may be overlapping, rather than identical.

Alternatively, the mechanism of synergy may be completely unrelated to the tubulin-binding properties of discodermolide, which was originally described in the literature as an immunosuppressant [43]. For example, discodermolide has been shown to modulate the expression of interleukin-2 receptors, which, in turn, regulate Fas-induced and nuclear factor κB-induced apoptosis, suggesting a hypothetical mechanism by which the synergy observed with Taxol and discodermolide could potentiate apoptosis [44].

At the present time, there is no information available on the antitumor activity of these new drugs in human tumors, and it will be of great interest to compare them to Taxol. The data herein suggest that Taxol and discodermolide may represent a synergistic drug combination that merits exploration.

REFERENCES

1. Schiff et al., Promotion of microtubule assembly in vitro by taxol. *Nature*, 277:665–67, 1979.
2. Rowinsky and Donehower, Paclitaxel (Taxol). *N. Engl. J. Med.*, 332:1004–14, 1995.
3. Rao et al., 3'-(p-azidobenzamido)taxol photolabels the N-terminal 31 amino acids of beta-tubulin. *J. Biol. Chem.*, 269:3132–34, 1994.
4. Rao et al., Characterization of the taxol binding site on the microtubule. 2-(m-Azidobenzoyl) taxol photolabels a peptide (amino acids 217–231) of beta-tubulin. *J. Biol. Chem.*, 270:20235–38, 1995.
5. Schiff and Horwitz, Taxol stabilizes microtubules in mouse fibroblast cells. *Proc. Natl. Acad. Sci. USA*, 77:1561–65, 1980.
6. Jordan et al., Mechanism of mitotic block and inhibition of cell proliferation by taxol at low concentrations. *Proc. Natl. Acad. Sci. USA*, 90:9552–56, 1993.

7. Jordan et al., Mitotic block induced in HeLa cells by low concentrations of paclitaxel (Taxol) results in abnormal mitotic exit and apoptotic cell death. *Cancer Res.,* 56:816–25, 1996.
8. Torres and Horwitz, Mechanisms of Taxol-induced cell death are concentration dependent. *Cancer Res.,* 58:3620–26, 1998.
9. Gottesman and Pastan, Biochemistry of multidrug resistance mediated by the multidrug transporter. *Annu. Rev. Biochem.,* 62:385–427, 1993.
10. Ter Haar et al., Discodermolide, a cytotoxic marine agent that stabilizes microtubules more potently than Taxol. *Biochemistry,* 35:243–50, 1996.
11. Hung et al., (+)-Discodermolide binds to microtubules in stoichiometric ratio to tubulin dimers, blocks taxol binding and results in mitotic arrest. *Chem. Biol.,* 3:287–93, 1996.
12. Kowalski et al., The microtubule-stabilizing agent discodermolide competitively inhibits the binding of Paclitaxel (Taxol) to tubulin polymers, enhances tubulin nucleation reactions more potently than Paclitaxel, and inhibits the growth of Paclitaxel-resistant cells. *Mol. Pharmacol.,* 52:613–22, 1997.
13. Balachandran et al., The potent microtubule-stabilizing agent (+)-discodermolide induces apoptosis in human breast carcinoma cells—preliminary comparisons to paclitaxel. *Anti-Cancer Drugs,* 9:67–76, 1998.
14. Bollag et al., Epothilones, a new class of microtubule-stabilizing agents with a Taxol-like mechanism of action. *Cancer Res.,* 55:2325–33, 1995.
15. Kowalski et al., Activities of the microtubule-stabilizing agents epothilones A and B with purified tubulin and in cells resistant to Paclitaxel (Taxol). *J. Biol. Chem.,* 272:2534–41, 1997.
16. Mann, J., Myxobacterial bounty. *Nature,* 385:117, 1997.
17. Su et al., Structure-activity relationships of the epothilones and the first in vivo comparison with Paclitaxel. *Agnew. Chem. Int. Ed. Engl.,* 36:2093–96, 1997.
18. Lindel et al., Eleutherobin, a new cytotoxin that mimics Paclitaxel (Taxol) by stabilizing microtubules. *J. Am. Chem. Soc.,* 119:8744–45, 1997.
19. McDaid et al., Structure-activity profiles of eleutherobin analogs and their cross-resistance in Taxol-resistant cell lines. *Cancer Chemother. Pharmacol.,* 44:131–37, 1999.
20. Long et al., Eleutherobin, a novel cytotoxic agent that induces tubulin polymerization, is similar to Paclitaxel (Taxol). *Cancer Res.,* 58:1111–15, 1998.
21. Rowinsky et al., Sequences of taxol and cisplatin: a phase I and pharmacologic study. *J. Clin. Oncol.,* 9:1692–1703, 1991.
22 Goldspiel, B. R., Clinical overview of the taxanes. *Pharmacotherapy,* 17:110S–125S, 1997.
23. Amadori et al., A phase I/II study of sequential doxorubicin and paclitaxel in the treatment of advanced breast cancer. *Semin. Oncol.,* 23:16–22, 1996.
24. Klaassen et al., Paclitaxel in combination with weekly 24-hour infusional 5-fluorouracil plus leucovorin in the second-line treatment of metastatic breast cancer: results of a phase II study. *Ann. Oncol.,* 9:45–50, 1998.
25. Felip et al., Superiority of sequential versus concurrent administration of paclitaxel with etoposide in advanced non-small cell lung cancer: comparison of two Phase II trials. *Clin. Cancer Res.,* 4:2723–28, 1998.
26. McDaid and Johnston, Synergistic interaction between paclitaxel and 8-chloro-adenosine 3', 5'-monophosphate in human ovarian carcinoma cell lines. *Clin. Cancer Res.,* 5:215–20, 1999.
27. Tortoriello et al., Phase I/II study of paclitaxel and vinorelbine in metastatic breast cancer. *Breast Cancer Res. Treat.,* 47:91–97, 1998.
28. Keren-Rosenberg and Muggia, Response to estramustine phosphate and paclitaxel in patients with advanced breast cancer: a phase I study. *Semin. Oncol.,* 24:S26–S29, 1997.
29. Hudes et al., Phase II trial of 96-hour paclitaxel plus oral estramustine phosphate in metastatic hormone-refractory prostate cancer. *J. Clin. Oncol.,* 15:3156–63, 1997.
30. Kavallaris et al., Taxol-resistant epithelial ovarian tumors are associated with altered expression of specific β-tubulin isotypes. *J. Clin. Invest.,* 100:1282–93, 1997.
31. Balog et al., Total synthesis of (−)-epothilone A. *Agnew. Chem. Int. Ed. Engl.,* 35:2801–03, 1996.
32. Su et al., Total synthesis of (−)-epothilone B: an extension of the Suzuki coupling method and insights into structure-activity relationships of the epothilones. *Agnew. Chem. Int. Ed. Engl.,* 36:757–59, 1997.
33. Meng et al., The total syntheses of epothilones A and B. *J. Am. Chem. Soc.,* 119:10073–92, 1997.
34. Chen et al., The total synthesis of eleutherobin: a surprise ending. *Agnew. Chem. Int. Ed. Engl.,* 37:789–92, 1998.
35. Haber et al., Altered expression of Mβ2, the class II β-tubulin isotype, in a murine J774.2 cell line with a high level of Taxol resistance. *J. Biol. Chem.,* 270:31269–75, 1995.
36. Lowry et al., Protein measurement with the folin phenol reagent. *J. Biol. Chem.,* 193:265–75, 1951.
37. Chou and Talalay, Quantitative analysis of dose-effect relationships: the combined effects of multiple drugs or enzyme inhibitors. *Adv. Enzyme Regul.,* 22:27–55, 1984.
38. Ojima et al., A common pharmacophore for cytotoxic natural products that stabilize microtubules. *Proc. Natl. Acad. Sci. USA,* 96:4256–61, 1999.
39. Cabral et al., Taxol-requiring mutant of Chinese hamster ovary cells with impaired mitotic spindle assembly. *J. Cell Biol.,* 97:30–39, 1983.
40. Hyams and Lloyd (eds.), *Microtubules* (New York: Wiley-Liss, Inc., 1994).
41. Giannakakou et al., Combinations of paclitaxel and vinblastine and their effects on tubulin polymerization and cellular cytotoxicity: characterization of a synergistic schedule. *Int. J. Cancer,* 75:57–63, 1998.
42. Giannakakou et al., A β-tubulin mutation confers epothilone resistance in human cancer cells. *Proc. AACR,* 40:1885, 1999.
43. Longley et al., Immunosuppression by discodermolide. *Ann. NY Acad. Sci.,* 696:94–107, 1993.
44. Haux et al., The role of interleukin-2 in regulating the sensitivity of natural killer cells for Fas-mediated apoptosis. *Cancer Immunol. Immunother.,* 48:139–46, 1999.
45. Beers and Berkow (eds.), *The Merck Manual of Diagnosis and Therapy,* 17th ed. (Whitehouse Station, N.J.: Merck Research Laboratories, 1999) 973–74, 976, 986, 988, 991.
46. Nerenberg et al., Total synthesis of the immunosuppressive agent (−)-discodermolide. *J. Amer. Chem. Soc.,* 115:12,621–12,622, 1993.
47. *Physicians' Desk Reference,* 54th ed. (Montvale, N.J.: Medical Economics Company, Inc., 2000) 307, 682.
48. Hall et al., The fractional inhibitory concentration (FIC) index as a measure of synergy. *J. Antimicrob. Chemother.,* 11(5):427–33, 1983.

All publications mentioned hereinabove are hereby incorporated in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method of treating neoplasia in a subject in need of treatment, comprising administering to the subject an amount of paclitaxel effective to treat the neoplasia, in combination with an amount of discodermolide effective to treat the neoplasia, wherein a synergistic antineoplastic effect results.

2. The method of claim 1, wherein the subject is a human.

3. The method of claim 1, wherein the neoplasia is a carcinoma, a lymphocytic leukemia, a myeloid leukemia, a malignant lymphoma, a malignant melanoma, a myeloproliferative disease, a sarcoma, or a mixed type of neoplasia.

4. The method of claim 3, wherein the carcinoma is breast cancer, colon cancer, lung cancer, ovarian cancer, or prostate cancer.

5. The method of claim 1, wherein administration is concurrent.

6. The method of claim 1, wherein administration is sequential.

7. The method of claim 1, wherein administration is alternate.

8. A synergistic combination of antineoplastic agents, comprising an effective antineoplastic amount of paclitaxel and an effective antineoplastic amount of discodermolide.

9. The synergistic combination of claim 8, wherein paclitaxel and discodermolide are combined in a single formulation.

10. The synergistic combination of claim 8, wherein a separate, individual formulation of paclitaxel is combined with a separate, individual formulation of discodermolide.

11. The synergistic combination of claim 8, which is useful in the treatment of neoplasia.

* * * * *